(12) United States Patent
Lindenberg

(10) Patent No.: US 7,781,207 B2
(45) Date of Patent: Aug. 24, 2010

(54) IN VITRO FERTILISATION

(75) Inventor: Svend Lindenberg, Skodsborg (DK)

(73) Assignee: Region Hovedstaden v/Herlev Hospital, Herlev (DK)

( * ) Notice: Subject to any disclaimer, the term of this patent is extended or adjusted under 35 U.S.C. 154(b) by 0 days.

(21) Appl. No.: 12/482,031

(22) Filed: Jun. 10, 2009

(65) Prior Publication Data

US 2009/0281370 A1 Nov. 12, 2009

Related U.S. Application Data

(63) Continuation of application No. 10/518,055, filed as application No. PCT/DK03/00401 on Jun. 17, 2003, now Pat. No. 7,547,541.

(60) Provisional application No. 60/407,686, filed on Sep. 4, 2002, provisional application No. 60/407,685, filed on Sep. 4, 2002.

(30) Foreign Application Priority Data

Jun. 17, 2002 (DK) ............................... 2002 00924
Jun. 17, 2002 (DK) ............................... 2002 00925

(51) Int. Cl.
C12M 1/00 (2006.01)
C12M 3/00 (2006.01)

(52) U.S. Cl. ..................................... 435/303.1; 600/35

(58) Field of Classification Search ................... 600/35; 424/93.7
See application file for complete search history.

(56) References Cited

U.S. PATENT DOCUMENTS

| | | | |
|---|---|---|---|
| 4,262,091 A | 4/1981 | Cox et al. | |
| 4,892,830 A | 1/1990 | Findley et al. | |
| 5,169,217 A | 12/1992 | Orchard et al. ............ | 312/223.1 |
| 5,219,215 A | 6/1993 | Akagawa et al. | |
| 5,730,777 A | 3/1998 | Petersen et al. | |
| 5,837,543 A | 11/1998 | Conway-Myers et al. | |
| 5,882,928 A * | 3/1999 | Moses ......................... | 435/375 |
| 6,050,935 A | 4/2000 | Ranoux et al. | |
| 6,110,741 A | 8/2000 | Hearn et al. | |
| 6,140,121 A * | 10/2000 | Ellington et al. ............ | 435/374 |
| 6,184,035 B1 | 2/2001 | Csete et al. | |
| 6,399,375 B2 | 6/2002 | Vajta .......................... | 435/374 |
| 7,094,527 B2 * | 8/2006 | Seidel et al. .................... | 435/2 |
| 2001/0028878 A1 | 10/2001 | Lindenberg | |
| 2001/0049829 A1 | 12/2001 | DeSousa et al. | |
| 2002/0068358 A1 * | 6/2002 | Campbell et al. ......... | 435/289.1 |
| 2004/0168341 A1 * | 9/2004 | Petersen et al. ............... | 34/402 |

FOREIGN PATENT DOCUMENTS

| | | |
|---|---|---|
| EP | 1 018 547 A1 | 7/2000 |
| WO | WO 94/19922 | 9/1994 |
| WO | WO 98/30676 A1 | 7/1998 |
| WO | WO 99/67364 | 12/1999 |
| WO | WO 99/67365 A1 | 12/1999 |
| WO | WO 00/32140 A1 | 6/2000 |
| WO | WO 00/38583 A1 | 7/2000 |
| WO | WO 01/64845 A1 | 9/2001 |
| WO | WO 01/94552 A2 | 12/2001 |

OTHER PUBLICATIONS

James W. Catt et. al., "Toxic effects of oxygen on human embryo development", *Human Reproduction*, vol. 15, (Suppl. 2), pp. 199-206, Jul. 2000.
James A. Thomson et. al., "Human embryonic stem cell and embryonic germ cell lines", *Trends in Biotechnology*, vol. 18, No. 2, pp. 53-57, Feb. 2000.
J. F. Griveau et. al., "Influence of oxygen tension on reactive oxygen species production and human sperm function", *International Journal of Andrology*, vol. 20, No. 4, pp. 195-200, Aug. 1997.
John J. Eppig et. al., "Factors Affecting the Developmental Competence of Mouse Oocytes Grown In Vitro: Oxygen Concentration", *Molecular Reproduction and Development*, vol. 42, No. 4, pp. 447-456, Dec. 1995.
Burkman L. J. A Microperfusion Chamber for study of Mammalian Spermatozoa. 1988. Journal of Andrology, v. 9, p. 102-108.
Kaneko S et al., "Development of Simple Oocyte/Embryo Handling Culture System.", Journal of Fertilization and Implantation (Japan), 1995, vol. 12, No. 1, pp. 89-91.
Olsen S. E. et al., "Reduced oxygen tension and EDTA improve bovine zygote development in a chemically defined medium.", Journal of Animal Science (2000), vol. 78, No. 1, pp. 152-157.

* cited by examiner

*Primary Examiner*—Walter D Griffin
*Assistant Examiner*—Shanta G Doe
(74) *Attorney, Agent, or Firm*—Iver P. Cooper

(57) ABSTRACT

The present invention relates to a method and a system for producing a mammalian pre-embryo and a stem cell having a better quality than prior art methods. The system comprises means for obtaining a mammalian oocyte, and means for obtaining a mammalian spermatozoa, and an apparatus having at least two separate air-tight chambers, for which the oxygen tension of one chamber may be changed independent of the oxygen tension of the other chamber, said at least two separate air-tight chambers constitute a main chamber and at least one residence chamber. The method for in vitro producing a mammalian pre-embryo comprising the steps: a1) providing a mammalian oocyte, a2) providing a mammalian spermatozoa, b) culturing the oocyte and the spermatozoa, c) fertilizing the oocyte with the spermatozoa obtaining a fertilized oocyte, and d) allowing cell-division of the fertilized oocyte obtaining a multicellular pre-embryo wherein at least one of the steps a1) or a2) is conducted at an oxygen tension below 15%, or e) allowing cell-division of the fertilized oocyte obtaining a multicellular pre-embryo, wherein the culture is performed at an oxygen tension allowing cultivation of the cells and wherein at least one of the steps comprises a change in the oxygen tension Stem cells are produced from the multicellular pre-embryo.

22 Claims, 3 Drawing Sheets

Embryo score n-Pn

Embryos scoring between 1.0 and 6.0

M

B1

B2

B3

Bn1
Bn2
Bn3

HB1

HB2

Fig. 2
Fig. 2a
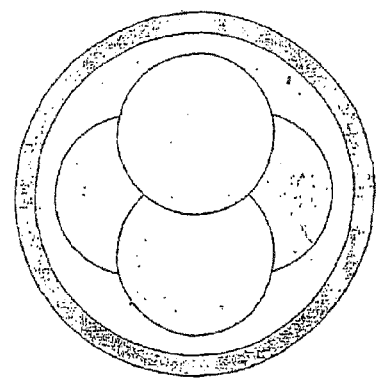
Fig. 2b
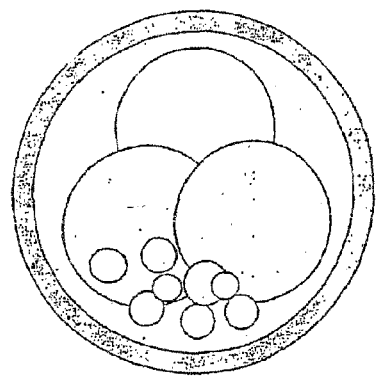
Fig. 2c
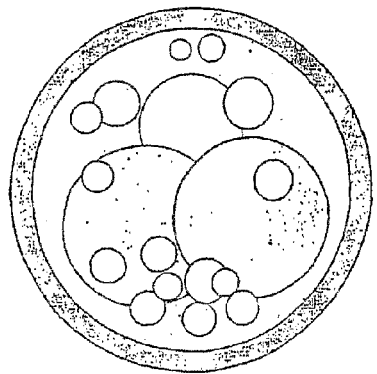
Fig. 2d
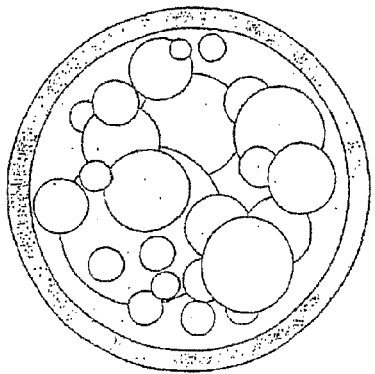

IN VITRO FERTILISATION

FIELD OF INVENTION

The present invention relates to in vitro co-culturing of oocytes and spermatozoa, in vitro fertilisation (IVF), and in vitro culturing of fertilised gametes, wherein the culturing conditions comprises lowered oxygen tension in the entire culturing period or lowered oxygen tension in periods of the culturing period or the culturing conditions comprises changed oxygen tension throughout the culturing period or changed oxygen tension in periods of the culturing period. The invention further relates to in vitro maturation (IVM) of immature oocytes or spermatozoa, co-culturing the matured oocytes with sperm cells to fertilise the eggs.

BACKGROUND OF INVENTION

In nature, fertilisation occurs by sperm cells being deposited into the female of warm-blooded animal species (including humans) and then binding to and fusing with an oocyte. This fertilised oocyte then divides to form an embryo. Over the last several decades, the use of assisted reproduction techniques has allowed scientists and clinicians to intervene in these events to treat poor fertility in some individuals or to store sperm, oocytes or embryos for use at other locations or times. In vitro fertilisation (IVF) involves collection of eggs e.g. by laparoscopy, followed by mixing eggs and sperm and culture of the embryos before transferring them to the uterine cavity of the female to continue their development. A recent innovation has been the introduction of the technique of intracytoplasmic sperm injection (ICSI), in which sperm are microinjected into the egg cytoplasm.

At each step of the way, in vitro intervention decreases the normal survival and function of sperm, oocytes, and embryos. Much research has been dedicated towards improving these procedures; however, overall success remains limited. For example, less than 20% of IVF attempts result in the birth of a child. Oocytes and embryos also show significantly disrupted function after culture. Thus, in spite of several decades of work, much room remains for improvement in the field of assisted reproduction technologies and especially in gamete and embryo handling, culture, and storage.

There is a particular need for improved culture conditions to support mammalian oocytes and embryos. A high percentage of embryos that are fertilised or transferred in vitro cease development prematurely. The consequences are felt at both the economic and the human levels. Many programs of fertility treatments for humans involve the in vitro fertilisation or transfer of oocytes or embryos. The success rates of human fertility treatments are not high. The low success rates impose substantial economic and emotional costs. Even incremental improvements in the success rate can be of substantial benefit. One of the many causes of the low overall success rate is the frequent failure of embryos to grow and develop properly in vitro. Improved culturing conditions to better support embryo growth can not only enhance the success rate of fertility treatments, but ironically can also reduce the rate of multiple pregnancies resulting from the treatments. Because the overall success rate of current methods is low, practitioners often implant multiple embryos to increase the likelihood of pregnancy. Implanting multiple embryos increases the likelihood of multiple pregnancies as well. If each individual embryo were more likely to survive, then the perceived need to implant multiple embryos simultaneously would decline, and the rate of multiple pregnancies would decrease.

Prior art describes different culture conditions. In U.S. Pat. No. 6,140,121 nitric oxide adversely affects survival and development of cells such as oocytes and embryos in vitro, particularly in a co-culture system. The addition of a nitric oxide inhibitor such as hemoglobin to such systems eliminates this toxic effect, and promotes mammalian oocytes, embryos, or other cells in vitro.

US application 20010028878 describes a method for in vitro maturation of a human oocyte by culturing an immature human oocyte in a cell culture medium for 10-30 hours. The maturation end point is metaphase II.

U.S. Pat. No. 6,140,121 describe methods and compositions to improve germ cell and embryo survival and function. Sperm, oocyte, and embryo survival and function is improved in vivo or in vitro by the use of a polysaccharide containing arabinose, galactose and/or hexuronic acid. In particular, a nonspermicidal lubricant containing such a polysaccharide (e.g., gum arabic, pectin, or galacturonic acid) increases the fertilisation potential of the sperm during coitus, artificial insemination or sperm collection. Similarly, a freezing medium containing a polysaccharide containing arabinose, galactose and/or hexuronic acid enhances sperm, oocyte, or embryo viability.

U.S. Pat. No. 6,110,741 describe Gonadotrophin releasor hormone-containing composition for embryo culture and method for in vitro fertilisation. In vitro incubation of primate embryos in the presence of added exogenous gonadotrophin releasor hormone (GnRH), results in enhanced chorionic gonadotrophin production associated with increased survival and attachment of the embryos. Treatment of in vitro fertilised embryos with GnRH can be used to improve implantation. Agonists of GnRH reduce attachment competence of embryos and are thereby useful as post-fertilisation contraceptives.

U.S. Pat. No. 6,050,935 describes an intravaginal fertilisation and culture container including a main chamber and a micro chamber.

U.S. Pat. No. 5,882,928 describe in vitro maturation and fertilisation of mammalian oocytes. An in vitro fertilisation method comprising culturing mammalian immature oocytes obtained from a mammalian ovary very early in the mammal's menstrual cycle in an oocyte maturation inhibitor-containing culture, removing the inhibitor and maturing and fertilising the oocytes to produce embryos for subsequent uterine-implantation. Preferably, the inhibitor is dbcAMP.

U.S. Pat. No. 5,837,543 describes a Human embryo co-culture system wherein an oocyte from a female is contacted with a monolayer of cultured human tubal epithelial cells; inseminating the oocyte; and transferring an embryo back to said female.

U.S. Pat. No. 5,730,777 describes an apparatus for performing operations under a gaseous atmosphere in a closed chamber comprising performing the operation in a housing comprising i) first chamber walls defining a first chamber containing a gaseous atmosphere and ii) second chamber walls defining a second chamber substantially enclosing the first chamber, the second chamber containing a gaseous atmosphere between the first and second chamber walls.

U.S. Pat. No. 4,892,830 describes an environmentally controlled incubator in which the enclosure of the incubator chamber strongly attenuates the transmission of light having wavelengths below about 500 nm for protecting biological materials within the chamber from toxic effects of short wavelength light. The incubator also includes sensors for determining the oxygen and carbon dioxide concentration within the chamber and means for adding carbon dioxide, nitrogen or oxygen to the ambient gas within the incubator ion order to maintain the desired levels of carbon dioxide and oxygen. It has been found that the normal oxygen concentration in air (21%) is toxic to mouse zygotes and pre-embryos. If the oxygen level is reduced to 5-10% however, this inhibition is not observed and the embryos continue to develop.

WO9830676 describes a method and incubator for cells and tissues, in particular sensitive cells and tissues, such as oocytes, fertilised oocytes and pre-implantation embryos, which require highly stable physical and chemical environment for in vitro development, are cultured in closed containers submerged or immersed in thermostatically controlled liquid baths, the containers being provided with an appropriate inner atmosphere containing, e.g. carbon dioxide, oxygen and humidity in appropriate levels WO9967364 describes a medium for the propagation of early stage embryos to blastocyst stage. The medium contains an effective amount of human GM-CSF to increase the percentage of pre-blastocyst embryos which develop to transfer ready blastocysts. Also it describes a method of growing early stage human embryos to transfer ready blastocysts. The method includes the step of incubating the embryos in vitro in a culture medium containing an effective amount of human GM-CSF for a time and under conditions to increase the proportion of transfer ready blastocysts. An IVF program that includes the method of growing early stage human embryos to transfer ready blastocysts is also described.

WO0032140 describes the following: Instead of immersing human reproductive cells in a single culture medium throughout the various procedures used in IVF, a process is provided by which the reproductive cells may be moved through a sequence of distinct culture media as the various IVF procedures are carried out.

SUMMARY OF INVENTION

The present invention relates to a method and a system for producing a mammalian pre-embryo having a better quality than prior art methods, whereby the probability of successful pregnancies with in vitro fertilisation using the pre-embryo obtained by the present method is increased. Also stem cells with an increased quality can be obtained by using the pre-embryo obtained by the present method.

The system for in vitro producing a mammalian pre-embryo comprises
- means for obtaining a mammalian oocyte, and
- means for obtaining a mammalian spermatozoa, and
- an apparatus having at least two separate air-tight chambers, for which the oxygen tension of one chamber may be changed independent of the oxygen tension of the other chamber, said at least two separate air-tight chambers constitute a main chamber and at least one residence chamber,
- said apparatus comprising at least one entrance port capable of communicating with the means for obtaining the mammalian oocyte and/or the mammalian spermatozoa, and
- an exit port for withdrawal of the pre-embryo, as well as
- a communication port between said at least two chambers allowing transfer of oocyte, spermatozoa and/or pre-embryo between the chambers.

In an aspect the system is used for culturing cell cultures. In principle all cell cultures can be cultured in said system, preferred is use of the system for culturing gametes, embryoes, blastocysts, stem cells and stem cell lines.

The system can be used in different ways to culture the cell culture. In one aspect the method for in vitro producing a mammalian pre-embryo comprising the following steps:
a1) providing a mammalian oocyte,
a2) providing a mammalian spermatozoa,
b) culturing the oocyte and the spermatozoa,
c) fertilizing the oocyte with the spermatozoa obtaining a fertilized oocyte, and
d) allowing cell-division of the fertilized oocyte obtaining a multicellular pre-embryo, wherein at least one of the steps a1) or a2) is conducted at an oxygen tension below 15%.

In another aspect the method for in vitro producing a mammalian pre-embryo comprises the following steps:
a) providing gametes selected from a mammalian oocyte and a mammalian spermatozoa,
b) culturing the oocyte and the spermatozoa,
c) fertilizing the oocyte with the spermatozoa obtaining a fertilized oocyte, and
e) allowing cell-division of the fertilized oocyte obtaining a multicellular pre-embryo, wherein the culture is performed at an oxygen tension allowing cultivation of the cells and wherein at least one of the steps comprises a change in the oxygen tension.

In an aspect the invention comprises a method for implanting a pre-embryo, comprising culturing oocyte and spermatozoa as described further herein, and transferring the resulting pre-embryo to the uterus of a mammalian female.

Furthermore the high quality pre-embryo may also be used for embryonal stem cell production. High quality embryos have cells with an increased amount of inner cell mass, leading to the development of an increased number of stem cells.

The method of producing a stem cell comprises:
a) Providing a multicellular pre-embryo as described herein,
b) isolating a multicellular pre-embryo of a),
c) isolating cells from the inner cell mass of the pre-embryo of b),
d) culturing said isolated cells from the inner cell mass in a matrix gel,
e) obtaining stem cells.

In an aspect is obtained stem cells obtained from multicellular pre-embryo obtained by the method described herein.

In an aspect is a stem cell wherein said stem cell is stabile in the sense no mutations or other genetic changes occur within the chromosomes or antigenesity on the surfaces of the cells.

Stem cells can develop into one or more stem cell lines. In an aspect a stem cell line is obtained from the stem cells produced by the method described herein.

Stem cell lines can be induced to produce different differentiated cells. It can thus be of importance to know the origin of the stem cell lines and the culture conditions for the cultures in said stem cell lines.

In an aspect is a stem cell package comprising:
Stem cells developed from the multicellular pre-embryo as described elsewhere herein,
Certificate describing the culture conditions for the stem cells and the cell cultures from which said stem cells are obtained.

DEFINITIONS

In the present context the term 'apoptosis' should be understood as a controlled cell death, where the cell itself destroys its nuclear DNA, envisioned by DNA stand-breaks.

In the present context the term 'blastomer' is the smaller cells occurring in the embryo following cleavage of the embryo.

In the present context the term 'blastocyst' and 'multicellular pre-embryo' is used interchangeable and is used to describe the embryo consisting of a cluster of cells following early cleavage of the fertilised egg, consisting of outer cells that have the potential to form placenta and an inner cell mass with the potential to form an embryo.

In the present context the term 'change in oxygen tension' means a condition where the oxygen tension is decreased or increased. Said change is performed due to the developmental stage of the cell either based on a visual or image determination or based on a knowledge to the time frame of the development of the cell culture or based on changes in the metabolism of the pre-embryo.

In the present context the term 'embryo' is the fertilised egg which constitute one cell with two pro-nucleus, or the fertilised egg has undergone cell division and constitute from two cells to a cell cluster.

In the present context the term 'gamete' is either an unfertilised egg from a female or a spermatozoon from a male.

In the present context the term 'implantation' means transfer of an embryo to the female uterus.

In the present context the term 'IVM' means 'in vitro maturation'.

In the present context the term 'IVF' means 'in vitro fertilisation'

In the present context the term 'lowered oxygen tension' means an oxygen tension below 15%.

In the present context the term 'MF-II' is an oocyte in the stage Metaphase of the second meiotic cell division. A MF-II oocyte has one polar body, expanded cumulus complex and has finally gone through a germinal vesicle break-down.

In the present context the term 'oocyte' is a gamete obtained from a female. The gamete may be immature or mature.

In the present context the term 'oxygen tension' is the concentration of oxygen within the gaseous phase of the tissue or of the surroundings of the cell culture systems.

In the present context the term 'oxygen tension unit' is used to describe the change in the oxygen tension, e.g. is a change from 3% to 5% a change of 2 units.

In the present context the term 'primary oocyte' is an immature oocyte. The oocyte is immature until it has finished the first meiotic division.

In the present context the term 'prophase II' is the stage of the prophase of the second meiotic division.

In the present context the term 'spermatozoa' is a gamete from a male. The spermatozoa may be immature or mature, in the latter stage it is capable of, by penetration, fertilising an oocyte.

In the present context the term 'stem cell' is an undifferentiated pluripotent or totipotent cell obtained from the inner cell mass of a blastocyst.

In the present context the term 'stem cell line' is a culture of cells obtained from stem cells, the stem cell line is stabile meaning it can be cultured for a period without undergoing changes. A stem cell line can be partly differentiated or undifferentiated i.e multipotent in the sense it can develop into some but not all kinds of cell types within the animal body or being totipotent thus capable of differentiate into all kinds of cell types.

In the present context the term 'zygote' is a fertilised egg or a 1-cell embryo.

In the present context the term 'zona pellucida' is the embryo shell.

DESCRIPTION OF DRAWINGS

FIG. 2 illustrates a cumulative embryo scoring (CES) system.

DETAILED DESCRIPTION OF THE INVENTION

Figure 1:
FIG. 1 illustrates an embryo scoring system based on Van Abbel et al.
Figure 1:
Figure 1:
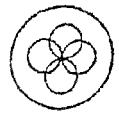
Figure 1:
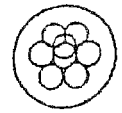
Figure 1:
Figure 1:
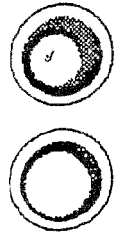
Figure 1:
Figure 1:
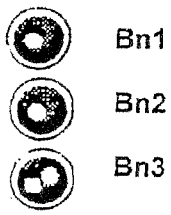
Figure 1:
Figure 1:

The following description discloses a method for in vitro producing a mammalian pre-embryo comprising the steps of a) providing gametes selected from a mammalian oocyte and a mammalian spermatozoa, b) culturing the oocyte and the spermatozoa, c) fertilising the oocyte with the spermatozoa obtaining a fertilised oocyte, and either d) allowing cell-division of the fertilised oocyte obtaining a multicellular pre-embryo, wherein at least one of the steps a), or b) is conducted at an oxygen tension below 15% or e) allowing cell-division of the fertilised oocyte obtaining a multicellular pre-embryo, wherein the culture is performed at an oxygen tension allowing cultivation of the cells and wherein at least one of the steps comprises a change in the oxygen tension. Said change in the oxygen tension comprises culturing the cell culture in at least two different oxygen tensions within a single step. The change in the oxygen tension is performed in accordance to the development stage of the cell culture as described elsewhere. In particular handling or observing the cell culture at the atmospheric oxygen tension is not the change in oxygen tension, which is the intention of the present invention.

By changing or lowering the oxygen tension of certain steps of the IVF procedure or changing or lowering the oxygen tension of all the IVF steps, an improvement of the quality of the gametes and of the embryos is obtained.

Culturing mammalian gametes, in vitro fertilised oocytes or embryos in conditions including the atmosphere with an oxygen concentration of 20-21%, is thought to hamper the gametes and eggs. Lowering the oxygen level to a level between 1% and 15%, or lowering the oxygen level to a level between 1% and 19% and changing the oxygen tension in one or all steps a), b), c) and e), it is the intention that a higher amount of the embryos may reach the blastocyst stage. One of the problems with human in vitro maturation and human in vitro fertilisation techniques is thought to be the activation and concentration of free reactive oxygen species preliminary generated from the high oxygen tension and supplemented during sperm preparation and in vitro fertilisations. By handling and culturing the gametes and embryos at lowered or changing oxygen tension, in combination with co-culturing the oocytes and spermatozoa we obtained an improvement of the IVF method, surprisingly the improvement of the IVF method was obtained without utilising co-culturing with feeder-cells.

In the invention as outlined above, one or more of the steps a), b), c) and d) may be performed at a lowered oxygen tension, whereas in the invention as outlined above, one or more of the steps a), b), c) and e) may be performed at a lowered or increased oxygen tension.

A preferred embodiment of the invention is the in vitro culture method as described wherein at least a part of step a) and at least one of the other steps are conducted at an oxygen tension below 15%. In one embodiment step a) and b) are performed at a lowered oxygen tension. A further preferred embodiment is said method wherein at least 3 of the steps a), b), c) and d) are conducted at an oxygen tension below 15%. In another embodiment of the invention, step a), b) and c) are performed at a lowered oxygen tension. In yet another embodiment of the invention, step b), c) and d) are performed at a lowered oxygen tension. In a further embodiment step a), c) and d) are performed at a lowered oxygen tension. In yet a further embodiment all step a), b), c) and d) are performed at a lowered oxygen tension.

Another preferred embodiment of said method is where the oxygen tension of step d) is higher as compared to the oxygen tension of any of the other steps b) and c).

A further preferred embodiment of said method is where all of the steps a), b), c) and d) and the transfer of the embryo to the uterus are conducted at an oxygen tension below 20%, such as 15%, such as below 13%, such as below 11%, such as below 10%, such as below 9%, such as below 8%, such as below 7%, such as below 6%, such as below 5%, such as below 4%, such as below 3%, such as below 2%, such as below 1%.

A preferred embodiment of the invention is the in vitro culture method as described herein where a change in the oxygen tension is performed in step a). Another preferred embodiment of the invention is the in vitro culture method as described herein where a change in the oxygen tension is performed in step b). A further preferred embodiment of the invention is the in vitro culture method as described herein where a change in the oxygen tension is performed in step c). Yet a further preferred embodiment of the invention is the in vitro culture method as described herein where a change in the oxygen tension is performed in step e).

A preferred embodiment of the invention is the in vitro culture method as described herein where a change in the oxygen tension is performed in step a) and step b). Another preferred embodiment of the invention is the in vitro culture method as described herein where a change in the oxygen tension is performed in step a) and step c). A further preferred embodiment of the invention is the in vitro culture method as described herein where a change in the oxygen tension is performed in step a) and step e). Yet a further preferred embodiment of the invention is the in vitro culture method as described herein where a change in the oxygen tension is performed in step b) and step c). Yet another preferred embodiment of the invention is the in vitro culture method as described herein where a change in the oxygen tension is performed in step b) and step e). A further preferred embodiment of the invention is the in vitro culture method as described herein where a change in the oxygen tension is performed in step c) and step e).

In particular in relation to maturation of oocytes a rise in the oxygen tension is preferred.

In an embodiment of the invention is the in vitro culture method as described herein where a change in the oxygen tension is performed in step a), b) and c). Another preferred embodiment of the invention is the in vitro culture method as described herein where a change in the oxygen tension is performed in step a), b) and e). A further preferred embodiment of the invention is the in vitro culture method as described herein where a change in the oxygen tension is performed in step a), c) and e). Yet a further preferred embodiment of the invention is the in vitro culture method as described herein where a change in the oxygen tension is performed in step b), c) and e).

A preferred embodiment of the invention is the in vitro culture method as described herein where a change in the oxygen tension is performed in all the steps a), b), c) and e).

In an embodiment the culture conditions include an oxygen tension which initially is selected to a level between 1% and 21%.

In an embodiment the change in the oxygen tension is a change to an oxygen tension below 20%, for example below 19%, such as below 18%, for example below 17%, such as below 16%, for example below 15%, such as below 14%, for example below 13%, such as below 12%, for example below 11%, such as below 10%, for example below 9%, such as below 8%, for example below 7%, such as below 6%, for example below 5%, such as below 4%, for example below 3%, such as below low 2%, for example below 1%.

In another embodiment the change in the oxygen tension is a change in the oxygen tension where it is lowered by at least 1 unit, such as at least 2 units, for example at least 3 units, such as at least 4 units, for example at least 5 units, such as at least 6 units, for example at least 7 units, such as at least 8 units, for example at least 9 units, such as at least 10 units, for example at least 11 units, such as at least 12 units, for example at least 13 units, such as at least 14 units, for example at least 15 units, such as at least 16 units, for example at least 17 units, such as at least 18 units, for example at least 19 units.

In yet another embodiment the change in the oxygen tension is a change in the oxygen tension where it is lowered by 1-19 units, such as 1-18 units, for example 1-17 units, such as 1-16 units, for example 1-15 units, such as 1-14 units, for example 1-13 units, such as 1-12 units, for example 1-11 units, such as 1-10 units, for example 1-9 units, such as 1-8 units, for example 1-7 units, such as 1-6 units, for example 1-5 units, such as 1-4 units, for example 1-3 units, such as 1-2.

In an embodiment the change in the oxygen tension is a change to an oxygen tension above 2%, for example above 3%, such as above 4%, for example above 5%, such as above 6%, for example above 7%, such as above 8%, for above 9%, such as above 10%, for example above 11%, such as above 12%, for example above 13%, such as above 14%, for example above 15%, such as above 16%, for example above 17%, %, such as above 18%, for example above 19%, such as above 20%, for example above 21%.

In another embodiment the change in the oxygen tension is a change in the oxygen tension where it is increased by at least 1 unit, such as at least 2 units, for example at least 3 units, such as at least 4 units, for example at least 5 units, such as at least 6 units, for example at least 7 units, such as at least 8 units, for example at least 9 units, such as at least 10 units, for example at least 11 units, such as at least 12 units, for example at least 13 units, such as at least 14 units, for example at least 15 units, such as at least 16 units, for example at least 17 units, such as at least 18 units, for example at least 19 units.

In yet another embodiment the change in the oxygen tension is a change in the oxygen tension where it is increased by 1-3 units, such as 2-5 units, for example 3-7 units, such as 4-9 units, for example 5-11 units, such as 6-13 units, for example 8-15 units, such as 10-18 units, for example 12-20 units.

In a preferred embodiment the oxygen tension followed a change as described above is regulated to a higher or lower level compared to the initially oxygen tension as described above. Thus the oxygen tension followed a change can be regulated to a level between 1% and 21%.

Monitoring and regulation of the oxygen tension may be conducted by any method known to persons skilled in the art.

Yet another preferred embodiment of said method is where the conditions include a rise in the oxygen tension followed by lowering the oxygen tension. Said rise of the oxygen tension is at least 2 units, and said rise of the oxygen tension is maintained for at least 30 minutes. In an embodiment the oxygen tension is at least 0.5% and maximum 20%. In particular when allowing maturation of the oocyte a rise in the oxygen tension is preferred.

In another embodiment the change in the oxygen tension is conducted for at least 1 minute, for example at least 2 minutes, such as at least 3 minutes, for example at least 4 minutes, such as at least 5 minutes, for example at least 6 minutes, such as at least 7 minutes, for example at least 8 minutes, such as at least 9 minutes, such as at least 10 minutes, for example at least 11 minutes, such as at least 12 minutes, for example at least 13 minutes, such as at least 14 minutes, for example at least 15 minutes, such as at least 16 minutes, for example at least 20 minutes, such as at least 30 minutes, such as at least 45 minutes, for example at least 1 hour, such as at least 1½ hour, for example at least 2 hours, such as at least 2½ hours, for example at least 3 hours, such as at least 4 hours, for example at least 5 hours, such as at least 6 hours, for example at least 7 hours, such as at least 8 hours, for example at least 9 hours, such as at least 10 hours.

In a preferred embodiment the changes of the oxygen tension can be performed one or more times in each of the steps a), b), c) and e) in the mentioned combinations and for duration as described above.

In an embodiment the duration of the changes mentioned above applies to each of the mentioned combinations of step a), b), c) and e) with a change in the oxygen concentration in one or more of the steps.

Yet another preferred embodiment of said method is where the oxygen tension is regulated in accordance to the phase or stage of the cell or cell structure and the condition or the quality of the oocyte or the embryo.

In an embodiment, the cell culture, as described herein include co-culture of female and male gametes in step b) of the invention. The co-culturing may be performed for at least 1 minute, such as at least 2 minutes, such as at least 5 minutes, such as at least 10 minutes, such as at least 30 minutes, such as at least 1 hour, such as at least 2 hours, such as at least 3 hours, such as at least 4 hours, such as at least 5 hours, such as at least 10 hours, such as at least 15 hours, such as at least 20 hours, such as at least 25 hours, such as at least 30 hours, such as at least 35 hours, such as at least 40 hours, such as at least 45 hours, such as at least 50 hours.

In another embodiment the change in the oxygen tension is conducted for at least 1 minute, for example at least 2 minutes, such as at least 3 minutes, for example at least 4 minutes, such as at least 5 minutes, for example at least 6 minutes, such as at least 7 minutes, for example at least 8 minutes, such as at least 9 minutes, such as at least 10 minutes, for example at least 11 minutes, such as at least 12 minutes, for example at least 13 minutes, such as at least 14 minutes, for example at least 15 minutes, such as at least 16 minutes, for example at least 20 minutes, such as at least 30 minutes, such as at least 45 minutes, for example at least 1 hour, such as at least 1½ hour, for example at least 2 hours, such as at least 2½ hours, for example at least 3 hours, such as at least 4 hours, for example at least 5 hours, such as at least 6 hours, for example at least 7 hours, such as at least 8 hours, for example at least 9 hours, such as at least 10 hours.

In a preferred embodiment the changes of the oxygen tension can be performed one or more times in each of the steps a), b), c) and e) in the mentioned combinations and for duration as described above.

In an embodiment the duration of the changes mentioned above applies to each of the mentioned combinations of step a), b), c) and e) with a change in the oxygen concentration in one or more of the steps.

The purpose of the co-culturing of oocyte and spermatozoa is improved fertilisation of oocyte by spermatozoa. Furthermore, the culture conditions are then identical for the oocytes and spermatozoa, which also possible leads to an improved fertilisation.

Gametes

The invention as described above may be performed with any kind of cells capable of participating in the formation of an embryo, examples of such cells comprises oocytes and sperm cells of a mammal. The mammalian oocyte and mammalian spermatozoa is gametes obtained from female and male, respectively, of a mammal. These mammals could be, but are not limited to humans, farming animals such as cows, pigs, horses, goats, sheeps, deers, other kinds of domestic animals, such as dogs, cats, experimental animals, such as rabbits, rats, mice, monkeys or animal races in the risk of extermination or threatened species including but not limited to tigers, lions, pandas, gorilla, whales, or other mammals where the pair creation is controlled by humans including but not limited to breeding of farming animals, breeding of domestic animals or pairing of animals living under conditions which inhibit the possibilities of the animals to find a mate, such as animals living in a zoo, especially to avoid any risk of inbreeding.

In a preferred embodiment the mammalian oocyte and mammalian spermatozoa are gametes obtained from cows. In another preferred embodiment the mammalian oocyte and mammalian spermatozoa are gametes obtained from pigs. In yet another preferred embodiment the mammalian oocyte and mammalian spermatozoa are gametes obtained from horses. In a most preferred embodiment the mammalian oocyte and mammalian spermatozoa are gametes obtained from humans.

Oocytes

In many cases, the oocytes as described above are obtained from a female patient who wishes to be pregnant, while the sperm cells are obtained from the male appearing to be her husband, or the gametes are obtained from female and male which constitute a couple. In some cases, however, it may be preferable to use cells from a donor either of a female or a male.

In a preferred embodiment the oocyte is obtained as an immature oocyte from the female ovarium. The oocyte is immature until shortly after it leaves the ovarium. In the ovarium of a female foetus the primary oocyte initiates the prophase of the first meiotic division, in this stage surrounding epithelial cells develop and a primordial follicle forms. The primordial follicle with the oocyt in the dictyotene stage between prophase and metaphase of the first meiotic division, constitute a resting stage from before birth to at least until puberty, or until the primordial follicle reenter the first meiotic division. The primary oocyte still in the dictyotene stage begins to increase in size and surrounding follicular cells change from flat to cuboidal as the stage of primary follicle is entered, followed by development of the zona pellucida between the oocyte and the follicular cells. A thick cellular layer begins to develop around the oocyte and the zona pellucida, inside of this cellular layer fluid filled spaces appear, when these spaces coalesce the antrum is formed. When the antrum reach its maximum size, the follicle is mature, also denoted tertiary follicle, Graafian follicle or Vesicular follicle, and it has reached a diameter of 6-12 mm. As soon as the follicle is mature, the primary oocyte resumes its first meiotic division, and the first meiotic division occurs shortly before ovulation. The secondary meiotic division starts immediately followed the first meiotic division, and the moment the secondary oocyte shows the spindle formation, ovulation occurs and the oocyte is shed from the ovary. At the time just before ovulation the mature follicle has a diameter of about 15 mm. The second melotic division is completed only if the oocyte is fertilised.

In another preferred embodiment the oocyte is obtained from a primary ovarian follicle, secondary ovarian follicle, preantral ovarian follicle, early antral follicles or antral follicles. A preferred embodiment of the invention is obtaining the oocyte in the dictyotene stage from the follicle in its late primordial stage or primary stage.

The normal ovulating woman will recruit approx. 300 of the immature oocytes described above for each menstrual cycle. This recruitment takes place before the actual cycle. At the day of menstruation, around 20-30 immature oocytes will still be present. Normally, during a process of apoptosis all but one oocyte will die before ovulation. At day 5-10 approx. 10-15 immature oocytes will be present in their small follicles being 10-12 mm in diameter. Some still growing and some starting to undergo an apoptotic process. Optionally the gametes to be used within this invention are derived from ovarian follicles with a diameter of about 8-12 mm. The advantage of such small follicles is that they are present in substantial numbers without severe hormonally treatment, they can be seen by ultrasound and an ultrasonically guided transvaginal puncture of the follicles is possible to perform in order to retrieve the oocyte.

The oocyte can be obtained from the ovarium by aspiration into a needle. Oocyt harvest is usually accomplished by one of two general methods. The first, ultrasound-guided aspiration, is a minor surgical procedure that can be done with intravenous analgesia. Usually, the ultrasound probe is inserted through the vagina. The probe emits high-frequency sound waves which are translated into images of the pelvic organs that are shown on a monitor screen. When a mature follicle is identified, the specialist guides a needle through the vagina and into the follicle. The egg is removed through the needle by a suction device. This is called aspiration. The needle may also be guided through the abdominal wall or through the bladder into the follicle. These approaches may be necessary if the ovary and its follicles are inaccessible using a needle introduced through the vagina. Laparoscopy is a surgical procedure usually requiring general anesthesia. In the operating room, a surgeon inserts a laparoscope, a long, thin tube much like a telescope, through an incision below or in the woman's navel. Looking through the laparoscope, the surgeon guides the needle through the abdominal wall into the ovarian follicle. The eggs and follicular fluid are then aspirated.

In another embodiment of the invention, the oocyte is obtained from the ovarium by removing part of or the entire ovarian tissue containing primary-, secondary or antral follicles and obtaining the containing primary-, secondary or antral follicles from said ovarian tissue. The oocyte can be obtained from the ovarian tissue just following removing the ovarian tissue from the female, and further matured until the stage for fertilisation. The oocyte can also be cooled or frozen followed isolation from the ovarina tissue and subsequent matured to the stage of fertilisation. The ovarian tissue removed from the female can be cooled or frozen before the oocytes are isolated from the tissue.

In a preferred embodiment, the needle utilised to harvest the oocyte is part of a syringe and the oxygen tension within said needle and said syringe is controlled. The needle and syringe can constitute an independent unit, easy to handle, and where the oxygen tension can be maintained at a defined pressure by a connection to a controlling unit. The syringe with the oocyte is transported to aseptic conditions where the oocyte is transferred to culture medium. The aseptic conditions can constitute a laminar air flow bench or a working area of an incubator. The oocyte can also be transferred to a culture container in a method where the needle of the syringe is stuck through a membrane of an incubator and the oocytes are then transmitted to the culture container without opening of the incubator. The needle and syringe can also be connected directly to the incubator. In this way the oocyte is transported directly from the ovarium through the needle and a tube to the culture container in the incubator. Accordingly, independently of method, it is preferred that the obtained oocyte is transferred under lowered oxygen tension.

In one embodiment the oocyte is obtained from a mammal subsequent to treatment of said mammal with hormones capable of maturing oocytes. In general, there is two times for harvesting oocytes. A harvest of multiple mature oocytes by treating the woman with hormones, or harvesting of immature oocytes without female hormone treatment followed by in vitro maturation of the oocytes. The method based on hormone treatment is as follows: During ovulation enhancement, drugs are used to induce the patient's ovaries to grow several mature eggs rather than the single egg that normally develops each month. This phase is often referred to as enhanced follicular recruitment or controlled ovarian hyperstimulation. Depending on the program and the patient, drug type and dosage varies. Most often, the drugs are given over a period of seven to ten days. Drugs currently in use, but not limited to include: clomiphene citrate, human menopausal gonadotropin (hCG), and a gonodotropin releasing hormone (GnRH) analog called leuprolide. Most of these drugs may be used alone or in a combination with others.

When the time to harvest oocyte is approaching, the development of ovarian follicles, which are fluid-filled sacs where eggs grow are monitored in a process where the ovaries are scanned frequently with ultrasound. Blood samples are drawn to measure the serum levels of estrogen and sometimes luteinizing hormone (LH). Estrogen production increases as the follicles develop. LH triggers ovulation. By interpreting the results of ultrasound and blood tests, the best time to harvest or remove the eggs is determined. When the follicles are almost mature, about a day and a half before ovulation would normally occur, an injection of human chorionic gonadotropin (hCG) is performed. Since ovulation should occur approximately 36 hours later, the use of hCG allows to control when ovulation will take place. The hCG simulates the woman's natural LH surge, which normally triggers ovulation. This surge also initiates changes in the eggs that allow fertilisation when the sperm are later introduced.

Also immature oocytes can be harvested and utilized in IVF. The advantages of starting with immature gametes are several. A woman in treatment for infertility normally undergoes a complicated hormonal treatment for many days for gaining a sufficient number of mature prophase II oocytes for in vitro fertilisation. This hormonal treatment encompasses pain, discomfort, stress, and risk of ovarian hyperstimulation syndrome, a condition feared among patients and doctors. This hormonal therapy is instituted to rescue immature oocytes which will otherwise undergo apoptosis. Thus, these hormones are essential for allowing the immature oocytes to mature within the ovary in the substantial number needed for IVF. If no hormones are administrated only one oocyte will mature as seen in normal ovulating women. By releasing these immature oocytes from the ovary prior to initiation of the apoptotic processes and mature them further in a clinical defined medium, the woman can avoid the risk and discomfort associated with hormonal treatment and still have a sufficient number of mature Metaphase II (MF-II) oocytes for subsequent IVF treatment.

In a preferred embodiment the hormone treatment as described above is performed with gonadotropins. Thus the treatment may involve exogenous or endogenous hormones, and other agents acting on the FSH or LH receptors. In another preferred embodiment said hormone is follicle-stimulating hormone (FSH). In yet another preferred embodiment said hormones is luteinizing hormone (LH). In a further embodiment the hormone is derivatives of FSH or LH or endogenous related hormones.

Cryopreservation

In one embodiment of the invention, the oocytes obtained as described above are stored for later use, this storage is a cryopreservation. When harvesting oocytes as described, multiple oocytes are obtained, not all of these oocytes are subjected to the fertilisation process immediately. In one embodiment the oocytes are subjected to cooling in a storage process at temperature below 20° C., such as below 10° C., such as below 5° C. In another embodiment the oocytes are subjected to freeze in a storage process at temperature below 0° C., such as about minus 40° C., such as about minus 80° C.

At the end of the IVF cycle there are often multiple embryos available for transfer, the surplus of these embryos can be stored as described above. It has been found that transferring more than four embryos carries a significant risk of multiple pregnancy, while it does not increase the singleton pregnancy rate proportionately. The advantage of cryopreservation is that there may be an increased chance of pregnancy occurrence without the necessity of multiple stimulation cycles and oocyte retrievals.

Embryos selected for cryopreservation can be frozen either on the day of fresh embryo transfer or a succeeding day up to four days later. The embryos can be placed in a cryopreserved media and frozen in a step-wise manner. At the end of cryopreservation procedure the embryos can be stored in liquid nitrogen.

Spermatozoa

In the IVF procedure as described above, spermatozoa is necessary to fertilise the oocyte. The spermatozoa obtained for use in the present invention may be immature spermatozoa, such as spermatides, primary spermatocytes, secondary spermatocytes, or mature spermatozoa. From one primary spermatocytes four spermatozoa can be obtained through the meiotic divisions comprising first and second meiotic division.

In an embodiment of the invention the spermatozoa is obtained from a male in an oxygen tension which is determined in accordance to the culture conditions to be utilised. Sperm cells or semen cells or spermatozoa from the male are frequently obtained by masturbation. Another method to harvest sperm cells are a surgical procedure, where a needle is guided to the testes of the man, and the sperm cells is aspirated into the needle. Yet another method is to obtain the spermatozoa by a machine stimulating the ejaculation and collecting the spermatozoa solution. The sperm can be separated from the seminal plasma in a process known as washing the sperm. In this process the sperm are mixed with a water-based solution in a test tube. The test tube is then placed in a centrifuge and spun at a high speed. The centrifuge force causes the heavier sperm cells to form a pellet beneath the fluid layer. The fluid layer is carefully removed and replaced with fresh solution. Over the next hour or so, some of the motile sperm swim up into the fluid layer. These sperm can be used to inseminate the eggs.

Collection of spermatozoa in male suffering from severe male infertility, immature sperm cells can be recovered either by needle biopsy or microsurgical techniques. The immature sperm cells and their surrounding Sertoli cell can because of an anti apoptotic activity in the medium benefit and mature the sperms. It is known that apoptosis in the testis is the major factor to detonate sperm function, specifically in the infertile man. In the males all sperm precursors possessing a tail will be recognised as immature until all cytoplasm has been stripped of and a final normal spermatozoa is recognised. Immature sperm cells can also be obtained from dead males of human or animals. Furthermore, if a patient is diagnosed with cancer, testicular or ovarian tissue can be dissected out and frozen prior to initiation of treatment that might cause sterility such as cytostatic or radiation treatment, with the object of later extracting immature gametes from the frozen tissue. These immature gametes can then be finally matured in a chemically defined medium.

In an embodiment the sperm cells has been subjected to cooling prior to utilization in the fertilisation process. In another embodiment the sperm cells has been subjected to freeze prior to utilization in the fertilisation process. The cooling and freezing processes are storage conditions giving the oppurtinities to make use of the spermatozoa at a later time.

IVM

The embodiment of the present invention relate IVF as well as IVM, see definitions above. In a preferred embodiment the invention relates to IVM. By in vitro maturation of a human gamete an immature human gamete is cultured in a cell culture medium. The human gamete could thus arise from a male as an immature spermatide or from a female as an immature oocyte. It is possible to obtain immature human gametes from women or men in infertility treatment by aspirating and extracting these gametes from ovarian or testicular tissue.

Oocytes can be harvested when they are in one of different stages followed by in vitro maturation (IVM). In an embodiment the immature gamete is derived from a follicle. In an embodiment said follicle is between 1 and 25 mm in diameter, such as between 2 and 18 mm, such as between 3 and 13 mm, such as between 5 and 12 mm, such as between 7 and 11 mm, such as between 8 and 10 mm.

In another embodiment the immature gamete is a primary oocyt. In yet another embodiment the immature gamete is in the prophase of the first meiotic division. In a further embodiment the immature gamete is in the dictyotene stage of the first meiotic division. In yet a further embodiment the immature gamete is in the late stage of the first meiotic metaphase. In another embodiment the oocyte is obtained from a primary follicle. In yet another embodiment the oocyte is obtained from a mature follicle.

In yet another embodiment the immature gamete is selected from primitive oogonia or later stage oocytes.

In an embodiment of the invention, the immature oocytes obtained from the ovary of the woman will be recognised as oocytes with a tight cumulus mass, no polar bodies or Germinal vesicles visible.

In a preferred embodiment the harvested immature gamete are cultured and matured up to metaphase II which is associated with a synchronised cumulus-, cytoplasm-, and nuclear maturation. Oocyte maturation is the final stage of oocyte development that prepares for fertilisation and embryo development. It can be divided into two general processes: nuclear maturation and cytoplasmic maturation. Nuclear maturation is defined as the resumption of meiosis and progression to MF-II while cytoplasmic maturation is defined as the extragenomic changes that prepare the egg for activation, pronuclear formation, and early embryogenesis. Thus, by an immature female gamete is understood an ova that upon contact with a mature sperm cell will not complete the mitotic division and thereby not accept the genetic material from the sperm cell and form a fertilised cell. By MF-II is understood an oocyte with 1 polar body, expanded cumulus complex and which has finally gone through a germinal vesicle break-down. These oocytes are readily recognised by a routine technician normally handling oocytes for IVF. In humans it has been possible to produce oocytes whose nuclear maturation has progressed to MF-II, but which are incompetent to complete preimplantation development. The in vitro maturation wherein culturing of the immature gamete from prophase to metaphase II can be completed within a period of 20 to 30 hours.

In this invention the criteria in determining cell-stages is not only the maturation stage of the nucleus, but also the cytoplasma and cumulus expansion. Another special feature of the present invention is that the maturation process is finished faster. Thus, culturing of the immature gamete from prophase to MF-II is completed within a period of 10 to 30 hours (such as 24 to 30 hours, i. e. 24 to 26 hours). This fast maturation can minimise the risks of failure in cumulus expansion and cytoplasm disorders. Further, it can minimise the exposure of the oocytes to longer culture time in vitro than necessary.

A chemically defined cell culture medium is used for the maturation process described above. The term "chemically defined medium" is to denote a medium without biologically extracted serum substances, and where all components and their concentration are known and described. The term "biologically extracted serum substances" includes substances such as immunoglobulins. Hormones such as growth hormones and gonadotrophins are not considered extracted from serum. If hormones or serum derived substances are to be added to the medium, recombinant hormones or serum derived substances are preferred.

The advantage of using a medium without biologically extracted serum substances is that the risk of transferring viruses or other pathogen or harmful particles to the medium and subsequently to the embryo is substantially reduced or non-existing. Furthermore, serum probably contains a factor, presently unknown, that inhibits the synchronised maturation of the nucleus, cytoplasma and cumulus expansion.

Thus, one aspect of the present invention relates to a method to avoid infection or contamination of a non-fertilisable gamete with known and/or unknown infectious agents (such as prions, viroids, virus, mycoplasma, bacteria, fungi) during in vitro maturation of the non-fertilisable gamete, by culturing the gamete in a medium without components originating from sources at least potentially containing infectious agents. In a preferred embodiment of that aspect, the method relates to avoiding contamination with toxic, teratogenic, carcinogenic, or mutagenic components.

Examples of media suitable for use in the present invention are: A medium containing at least one factor that is capable of synchronising nuclear-, cytoplasma-, and cumulus cells maturation. In a preferred embodiment, the medium contains synthetic lipid or lipid precursor, such as sterol or metabolically acceptable derivatives thereof. This could be cortisone. The advantages of using these compounds are to stabilise cell membranes, provide precursors for membrane building, and as a substance to be involved in local paracrine steroid production within the cumulus oocyte complex. Cortisone or derivatives can also be directly involved in stimulating and synchronising the final maturation of these immature oocytes.

The basic culture medium should be one that can both support the oocyte as well as its cumulus cells. It is well known in the art that addition of gonadotropins and/or steroid such as E2 to the maturation medium enhances the fertilisability and/or developmental ability of e. g. cattle, monkey, and human oocytes. The addition of the gonadotrophins (FSH and hCG) to human IVM medium has been widely used but their optimal concentrations (or absolute necessity) have not been fully characterised. The cumulus cells can be considered a type of c-culture and as with other types of somatic cells, they generally require moderately high protein levels in the medium. It has been suggested that oocytes need to be primed with oestrogen in order to develop Ca++ oscillations. The medium of the present invention thus preferably contains oestrogens in concentrations of 0.1 to 10.mu.g/mL estradiol 17-.beta., e. g. 0.3 to 3 .mu.g/mL estradiol 17-.beta., preferably 1 .mu.g/mL estradiol 17-.beta.

In a much preferred embodiment of the present invention, the chemically defined medium among other factors contains ATA (Aurin Tricarboxylic Acid) as an antiapoptotic agent. The advantage of ATA is that it might provide optimal conditions to inhibit apoptotic processes otherwise deteriorating the oocyte maturation. Another advantage of the presence of ATA is that it allows the concentration of serum derived products, such as HSA or BSA to be lowered, such that the concentration of the serum derived products is zero.

The usage of an anti-apoptotic agent is preferred due to the fact that the oocyte retrieved already can have engaged in an apoptotic process in the cumulus mass. When apoptosis starts in the oocyte-cumulus complex, this will signal the start of maturation.

However, as this process progresses in the normal ovary, it will induce apoptosis in the oocyte. By removing the oocyte from the ovary after initiation of the apoptotic signal, which induces start of maturation, full development will take place in the chemically defined medium with e. g. ATA to stop further apoptosis.

The medium could be a medium as described in PCT/EP97/06721 hereby incorporated by reference. As an additive to the medium, is used the additives described in EP1090300 or WO9967365, these are denoted Medi-Cult SSR 4x, Medi-Cult SSR 4xa, Medi-Cult SSR 4xb, Medi-Cult SSR1 or Medi-Cult SSR2. As the basic medium, the preferred medium is Medi-Cult BBEM as described in EP1090300.

Apart from the contents of the medium, other factors are important in achieving fertilisable oocytes when cultured in vitro. These factors include the timing of the oocyte aspiration and the size of the follicles by the time of aspiration. An early apoptotic phase or an artificial plateau phase in the follicular growth may mimic the final preovulatory follicular maturation terms of developmental competence.

In vitro maturation of mammalian oocytes is not only related to growth of the follicle, but also to the size of the follicles and the oocytes. The human oocyte appears to have a size dependant ability to resume meiosis and complete maturation. A decreased maturation rate and cleavage rate of oocytes obtained from follicles <8 mm is observed, These results suggest that capacity of human oocyte maturation is closely correlated with follicular maturation. As mentioned above, the maturing oocytes retrieved are in an early apoptotic phase. Thus, with increasing size of the oocytes the risk of obtaining oocytes in a late apoptotic phase, that is close to dead cells, increases. Based on these experiences, the preferred size of the oocytes retrieved is less than 12 mm.

In an embodiment of the invention the in vitro maturation are performed at an oxygen tension below 20%, such as below 15%, for example below 13%, such as below 11%, for example below 10%, such as below 9%, for example below 8%, such as below 7%, for example below 6%, such as below 5%, for example below 4%, such as below 3%, for example below 2%, such as below 1% or under conditions described elsewhere herein.

In another embodiment of the invention the in vitro maturation are performed at a lowered oxygen tension as described above. One culture condition is further a temporal rise in the oxygen tension, where the rise is at least a 1 unit rise in the oxygen tension, such as at least 2 units, for example at least 3 units, such as at least 4 units, for example at least 5 units, such as at least 6 units, for example at least. 7 units, such as at least 8 units, for example at least 9 units, such as at least 10 units, for example at least 11 units, such as at least 12 units, for example at least 13 units, such as at least 14 units, for example at least 15 units.

In yet another embodiment the rise in the oxygen tension is a maximum of 15 units, for example maximum 14 units, such as maximum 12 units, for example maximum 11 units, such as maximum 10 units, for example maximum 9 units, such as maximum 8 units, for example maximum 7 units, such as maximum 6 units, for example maximum 5 units, such as maximum 4 units, for example maximum 3 units, such as maximum 2 units, for example maximum 1 units.

In a further embodiment the rise in the oxygen tension is 1-15 units, such as 1-12 units, for example 1-10 units, such as 1-8 units, for example 1-7 units, such as 1-6 units, for example 1-5 units, such as 1-4 units, for example 1-3 units, such as 1-2 units.

In general the rise in oxygen tension is conducted for at least 5 minutes, such as at least 10 minutes, for example at least 20 minutes, such as at least 30 minutes, such as at least 45 minutes, for example at least 1 hour, such as at least 1½ hour, for example at least 2 hours, such as at least 2½ hours, for example at least 3 hours, such as at least 4 hours, for example at least 5 hours, such as at least 6 hours, for example at least 7 hours, such as at least 8 hours, for example at least 9 hours, such as at least 10 hours.

The media discussed above may also be used for culturing immature sperm precursor cells from the testis.

IVM is further described in WO 9967365 and US application 20010028878.

In an embodiment of the invention, immature spermatozoa are cultured to maturity. This in vitro maturation of spermatozoa is performed at an oxygen tension below 20%, such as below 15%, for example below 13%, such as below 11%, for example below 10%, such as below 9%, for example below 8%, such as below 7%, for example below 6%, such as below 5%, for example below 4%, such as below 3%, for example below 2%, such as below 1%.

In another embodiment of the invention the in vitro maturation of spermatozoa are performed at a lowered oxygen tension as described above. One culture condition is further a temporal rise in the oxygen tension, where the rise is at least a 1 unit rise in the oxygen tension, such as at least 2 units, for example at least 3 units, such as at least 4 units, for example at least 5 units, such as at least 6 units, for example at least 7 units, and the rise in oxygen tension is conducted for at least 5 minutes, such as at least 10 minutes, for example at least 20 minutes, such as at least 30 minutes, such as at least 45 minutes, for example at least 1 hour, such as at least 1½ hour, for example at least 2 hours, such as at least 2½ hours, for example at least 3 hours.

Fertilisation

When oocytes are harvested they can be conducted to in vitro maturation as described above, cultured for a period or be fertilised immediately. In an embodiment of the invention these cultures are performed at an oxygen tension below 20%, such as below 15%, for example below 13%, such as below 11%, for example below 10%, such as below 9%, for example below 8%, such as below 7%, for example below 6%, such as below 5%, for example below 4%, such as below 3%, for example below 2%, such as below 1%.

In another embodiment of the invention the cultures are performed at a lowered oxygen tension as described above.

An example of the above described change in the oxygen tension is an oocyte which is cultured at an oxygen tension of 5%, the oxygen tension is increased to 15% for a period, and then lowered to 12%.

The harvested eggs are examined in a laboratory and each is graded for maturity as described below. The maturity of an egg determines when the sperm will be added to it (fertilisation). Fertilisation can be done immediately upon harvest, after several hours, on the following day, or after maturation of immature oocytes.

In a preferred embodiment of the invention the oocytes and spermatozoa are co-cultured that is cultured together in a culture dish. In another embodiment the co-culturing can be conducted with feeder cells. These co-culturing either with or without feeder-cells can be performed at an oxygen tension below 20%, such as below 15%, for example below 13%, such as below 11%, for example below 10%, such as below 9%, for example below 8%, such as below 7%, for example below 6%, such as below 5%, for example below 4%, such as below 3%, for example below 2%, such as below 1%.

In an embodiment of the invention the co-culture with or without feeder cells performed at a lowered oxygen tension further include a temporal rise in the oxygen tension, where the rise is at least a 1 unit rise in the oxygen tension, such as at least 2 units, for example at least 3 units, such as at least 4 units, for example at least 5 units, such as at least 6 units, for example at least 7 units, and the rise in oxygen tension is conducted for at least 30 minutes, such as at least 45 minutes, for example at least 1 hour, such as at least 1½ hour, for example at least 2 hours, such as at least 2½ hours, for example at least 3 hours.

A number of 5,000 to 500,000 sperms per egg are co-cultured. It can take about 18 hours for fertilisation to be completed, and about twelve hours later the fertilised cell or pre-embryo divides into two cells. After 48 hours, when pre-embryos usually consist of two to four cells each, they are ready to be placed into the woman's uterus. This procedure is known as embryo transfer.

In a preferred embodiment the fertilisation is conducted at an oxygen tension below 20%, such as below 15%, for example below 13%, such as below 11%, for example below 10%, such as below 9%, for example below 8%, such as below 7%, for example below 6%, such as below 5%, for example below 4%, such as below 3%, for example below 2%, such as below 1%.

In an embodiment of the invention the fertilisation performed at a lowered oxygen tension further include a temporal rise in the oxygen tension, where the rise is at least a 1 unit rise in the oxygen tension, such as at least 2 units, for example at least 3 units, such as at least 4 units, for example at least 5 units, such as at least 6 units, for example at least 7 units, and the rise in oxygen tension is conducted for at least 30 minutes, such as at least 45 minutes, for example at least 1 hour, such as at least 1½ hour, for example at least 2 hours, such as at least 2½ hours, for example at least 3 hours.

In a preferred embodiment the culturing of oocyte and spermatozoa includes a step for culturing said immature oocyte under conditions allowing maturation of the oocyte. Said conditions include an oxygen tension below 15%, such as below 13%, such as below 11%, such as below 10%, such as below 9%, such as below 8%, such as below 7%, such as below 6%, such as below 5%, such as below 4%, such as below 3%, such as below 2%, such as below 1%. The oxygen tension is chosen and changed during the culturing in accordance to the optimal in vitro conditions, but also in consistence with the stage and quality of the oocyte.

The IVF method concerns with the stages of embryogenesis from oocyte to embryos.

The oocyte is the unfertilised egg. The oocyte is sifting in the middle of a mass of follicular cells that act to protect the egg itself as it moves down the fallopian tube. To reach the egg, sperm must first penetrate this mass (called the cumulus) and then they must bore through the rubbery coat that directly surrounds the egg.

The fertilised egg is also called a zygote or 1-cell embryo. The egg is enclosed in zona pellucida. Within the egg, are two smaller concave-looking spherical objects—each of these is a 'pro-nucleus' contributed by one parent or the other and containing the parental DNA. Within the zona pellucida spherical objects called 'polar body' can be observed. The polar body is extruded from the egg proper after fertilisation with a second portion of maternal genetic material.

The first cell division takes place a day after fertilisation, resulting in the 2-cell embryo. From the 1-cell stage of embryogenesis all the way down to the blastocyst stage, the embryo is floating freely without a source of nutrients and it is physically constrained within the zona pellucida. So during this entire period, the embryo remains the same size.

Once again, each of the cells in the embryo divides, resulting in the 4-cell embryo. At this stage, it is still possible for each individual cell to become an entire human being. If the embryo breaks apart into its four cells at this stage, four identical quadruplets could develop to birth. Although a rare event, there are many known cases.

In the 8-cell embryo, differentiation has still not taken place. Each cell could become an entire human being (in theory). Therefore, any cell can be removed at this point for genetic diagnosis without any effect on the development of the remaining embryo.

In the blastocyst, the embryo now has about 64 cells. The cells are no longer equivalent. The embryo now has a fluid-filled cavity and a portion of the embryo called the inner cell mass lies on the side of the cavity. The half-dozen cells of the inner cell mass are the only ones that will be used to develop the fetus and child. The remaining cells, the outer cells or surface cells called the trophectoderm, help to form the placenta.

ICSI

In an embodiment of the invention the oocyte is fertilised with the spermatozoa by Intracytoplasmic sperm injection (ICSI). Intracytoplasmic sperm injection is also known as direct injection of spermatozoa (sperm) into the cytoplasm of the oocyte (DISCO), this method can be applied for the purposes of assisting fertilisation in human patients. The technique combines in vitro fertilisation with microinjection technology. A female oocyte (egg) is harvested and suitably prepared, a single sperm is isolated from a prepared sample into a microinjection needle, and the sperm is then injected into the ooplasm of the oocyte. In the methods of intracytoplasmic sperm injection (ICSI), the mature egg is held with a specialized holding pipette. Then very delicate, sharp and hollow needle is used to immobilize and pick up a single sperm. This needle is then carefully inserted through the zona of the egg and in to the cytoplasm of the egg. The sperm is injected in to the cytoplasm and the needle carefully removed. The eggs are checked the next morning for evidence of normal fertilisation.

The importance of cytoplasmic control over developmental competence has been described in the immature monkey oocyte. Using micromanipulation, ooplasm was removed from MF-II oocytes and injected into prophase I oocytes. Monkeys receiving the oocytes with cytoplasmic transfusion had a sevenfold increase in pregnancy rate compared to oocytes without ooplasm injection.

In an embodiment of the invention the oocyte fertilised by ICSI is cultured at an oxygen tension below 20%, such as below 15%, for example below 13%, such as below 11%, for example below 10%, such as below 9%, for example below 8%, such as below 7%, for example below 6%, such as below 5%, for example below 4%, such as below 3%, for example below 2%, such as below 1%.

Embryo Stages

An embodiment of the invention is culturing the fertilised oocyte to an embryo stage ready for transfer to the female uterus. This is obtained after at least ½ day culture following fertilisation of the oocyte, such as at least 1 day, for example at least 2 days, such as at least 3 days, for example at least 4 days, such as at least 5 days, such as at least 6 days, for example at least 7 days, such as at least 8 days, for example at least 9 days.

The embryo ready to transfer to the uterus can be the two-cell stage, the four-cell stage, the six-cell stage, the eight-cell stage, the morula stage, or the blastocyst stage, the blastocyst stage, where zona pellucida is disappeared, or a stage where the zona pellucida (embryo shell) of said embryo is opened to help the embryo hatch before implantation into the uterus. In each of these stages fragments of cell debris can be removed from said embryo, and thereby improving the quality of the embryo.

There are three embryonic cell types, which eventually give rise to the entire embryo and its associated tissue, these three cell types present in the very early embryo just before implantation or at the time of implantation are:
  Epiblast cells, which are stem cells that can self renew or differentiate into all the cell types of the embryo,
  Hypoblast cells which give rise to a protective membrane around the embryo (yolk sac) and
  Trophectoderm cells that develop first into a reservoir of cells which can self replicate and which generate a range of specialised cells that form much of the placenta.

In a preferred embodiment the fertilised oocyte is cultured to an embryo stage ready for transfer to the female uterus as described above, said culturing is performed at an oxygen tension below 20%, such as below 15%, for example below 13%, such as below 11%, for example below 10%, such as below 9%, for example below 8%, such as below 7%, for example below 6%, such as below 5%, for example below 4%, such as below 3%, for example below 2%, such as below 1%.

In a preferred embodiment the fertilised oocyte is cultured for 2-3 days at an oxygen tension below 13% or at an oxygen tension changing between 1% and 21% and to a stage of 4 cells before transferred to the female uterus.

In an embodiment of the invention the zona pellucida is opened by assisted hatching using either laser, mechanical force or acid tyrode before the embryo is transferred to the female uterus.

The "quality" of embryos can be assessed in accordance to different scoring systems. The scoring is determined by size of inner cell mass. Also the scoring is determined by components such as cell number, cell regularity (regularity of size), and degree of fragmentation. There are also other things that are noted about the embryos appearance, such as multi-nucleation, presence of vacuoles, granularity, thickness of the shell around the embryo, etc. In particular, also total cell number in blastocyst is a quality score.

In one scoring system the determinations of "quality" are not made until about 48 hours (or later) after the fertilisation of the egg. By 48 hours ("day 2"), it is preferred that at least some of the embryos are at least 3 cells—and preferably 4 cells or more. They must be at least 2 cells by then—or they have basically "arrested". By 72 hours ("day 3"), it is preferred that some of the embryos are at least 6 cells—and preferably at least a few embryos that have 7 cells or more. A fast development is not a necessity for success, babies has been observed that came from an embryo as slow as a 4 cell on day 3, but the chances for pregnancy increase greatly as the cell number increases.

Embryos with higher cell numbers and regular appearing cells (blastomeres) and little or no fragmentation have a higher overall chance of implanting than do their counterparts with less cells, more irregularity and more fragmentation.

Embryo quality as seen it under the microscope in the IVF lab gives some reasonable ability to predict the chances for pregnancy from an embryo transfer. However, because there are many other contributing factors involved that can not be measured, these generalizations do not always apply. Some cycles fail after transferring 3 perfect looking embryos, and also beautiful babies born after transferring low grade embryos is seen. The true genetic potential of the embryo to continue development and the quality and receptivity of the uterine lining are really impossible to measure.

Another important variable that can be overlooked is the embryo transfer technique itself. A smooth transfer with no trauma to the endometrial lining is essential to give the embryos the best chance for continuing with normal development.

Ultimately, the only true test of embryo quality is whether it implants and develops normally and eventually goes home from the hospital with mom. In other words, embryo grading systems are very imperfect, and a pregnancy test is normally needed to tell more about "quality" than the microscope can reveal.

Most IVF clinics "grade" each embryo using one of many scoring systems, of which a few that may be used according to the invention is described below.

It is important to evaluate and categorise human oocytes, fertilised ova and cleaved embryos during advanced fertility treatments due to the fact, that different developmental stages can be utilised for different procedures etc. One embryo score system which can be utilised in this invention is in accordance with the score system of Van Abbel et al. (1992) and Ziebe et al., (1997):

In this grading system the embryo is evaluated in accordance to the cleavage stage (=blastomer number) and the amount of anuclear fragments is scored with morphological criteria. The embryo at the stage of two cells till the morula stage can obtain a score in accordance to the following list of the morphological criteria:

Score 1.0: Equally-sized symmetrical blastomers, no anuclear fragments.
Score 2.0: Uneven sized blastomers, no anuclear fragments.
Score 2.1: Embryos with less than 10% fragmentation.
Score 2.2: Embryos with 10-20% blastomeric fragmentation.
Score 3.0: Embryos with 20-50% blastomeric fragmentation.
Score 3.2: Embryos with more than 50% blastomeric fragmentation.
Score 4.0: Totally fragmentised.
Score 5.0: Fertilised, not separated.
Score 6.0: Not fertilised, not separated.
M: Morula.
B1: Early blastocyst.
B2: Expanding blastocyst.
B3: Expanded blastocyst.
Bn1: Normal cavity, normal cells.
Bn2: Normal cavity, granular or dark cells.
Bn3: Anormal cavity.
HB1: Hatching blastocyst.
HB2: Hatched blastocyst.

In an embodiment of the invention the culturing of the embryo result in an embryo with 3-5 blastomers and the score selected among 1.0; 2.0; 2.1 and 2.2

In another embodiment of the invention the culturing of the embryo result in an embryo with 4 blastomers and the score selected among 1.0; 2.0 and 2.1.

It has been suggested, that not alone the stage of the embryo and the degree of fragmentation are important for selection of embryos. Also the following has to be taken into account: 1) the thickness and variability of the thickness of the zona pellucida. Not only is zona hardening due to the in vitro conditions a problem for the embryo. A thin or variable thinning of the zona pellucida might be associated with a better pregnancy chance. This is probably because the trophoblastic cell can better penetrate a thin zona during hatching then a thick hard zona. 2) the type and distribution of the fragments. An even distribution of fragments in an embryo might disturb several junctions between all blastomeres and hereby jeopardise the function of the embryo. If fragments are assembled in one area this disturbance of the embryo is not that severe. 3) the timing of the cleavages of the embryo. The fastest normal dividing embryo may also possesses the best chance of giving offspring. In accordance to this, the best embryos for transfer will be the embryos with the lowest score according to Van Abbel, the embryo has cleaved normally according to the time of transfer (i.e. 4-cells for transfer at day 2 post fertilisation), a variable thickness of the zona pellucida, and if fragments are present, than choose embryos with localised fragments.

In another scoring system the embryos transferred to the female uterus obtain a cumulative embryo score (CES) (Joesbury et al., 1998). In this scoring system the embryos are graded on the second day following fertilisation and just prior to transfer. Grading is based on granularity and symmetry of the blastomers, fragmentation and rate of development. A hypothetically perfect embryo is graded a maximum of 4.0 points with 0.5 or 0.1 point deducted in accordance with the degree of deviation from the optimum for each morphological parameter.

A zygote is graded 1 point.
An embryo with equally sized and symmetrically blastomers is graded 4 points.
An embryo with unequally sized blastomers and less than 10% fragmentation is graded 3 points.
An embryo with 10-50% fragmentation is graded 2 points.
An embryo with more than 50% fragmentation is graded 1 point.

The score of each embryo is obtained by multiplying the grade of each embryo selected for transfer by the number of blastomers of that embryo.

Embryos developing faster than the 'ideal' growth rate can have pregnancy outcomes that are poorer than embryos that exhibit a 'normal' growth pattern. To account for the potential inferiority of fast-developing embryos, the calculation of CES is performed by an embryo at the 5-cell stage award 3 points for number of cells and for 6-, 7-, or 8-cell embryo 2 points for number of cells are awarded.

The highest scoring embryos are selected for uterine transfer. The collective quality of embryos selected for transfer is based on the cumulative embryo score (CES), which entail multiplying the score of each embryo selected for.

In an embodiment of the invention the embryos are cultured to a 3-5 cell stage with 10-50% fragmentation, thus the embryo is awarded 6-7 points.

In another embodiment of the invention the embryos are cultured to a 3-5 cell stage with less than 10% fragmentation, thus the embryo is awarded 7-8 points.

In a preferred embodiment of the invention the embryos are cultured to a 4 cell stage with less than 10% fragmentation, thus the embryo is awarded 8 points In a third scoring system, a Graduated Embryos Score (GES) is obtained for each embryo (Fisch et al,. 2001). The GES system awards a total possible score of 100 points, based on three evaluations occuring at 16-18, 25-27 and 64-67 hours post fertilisation.

First evaluation, 16-18 h:
Nucleoli aligned along pronuclear axis award a score of 20.
Second evaluation, 25-27 h:
Cleavage regular and symmetrical award a score of 30
Fragmentation absent award a score of 30.
Fragmentation less than 20% award a score of 25.
Fragmentation above 20% award a score of 0.
Third evaluation, 64-67 h:
7 cells, grade I or 8 cells, grade I or 8 cells, grade II or 9 cells, grade I award a score of 20.
7 cells, grade II or 9 cells, grade II or 10 cells, grade I or 11 cells, grade I or compacting, grade I award a score of 10.

Where grade I is symmetrical blastomers and absent fragmentation, grade II is slightly uneven blastomeres and less than 20% fragmentation.

The score of each evaluation time is multiplied for an embryo yielding a total score for said embryo. The maximum score of an embryo is 100.

In an embodiment of the invention, the embryos are cultured to a 7-9-cell embryo 64-67 hours after fertilisation and obtain the score of 60-100 according to the GES scoring system.

In another embodiment of the invention, the embryos are cultured to an embryo of 7 cells, grade I or 8 cells, grade I or 8 cells, grade II or 9 cells, grade I 64-67 hours after fertilisation and obtain the score of 70-100 according to the GES scoring system.

In a preferred embodiment of the invention, the embryos are cultured to an embryo of 7 cells, grade I or 8 cells, grade I or 8 cells, grade II or 9 cells, grade I 64-67 hours after fertilisation and obtain the score 80-100 according to the GES scoring system.

Any other scoring system correlating embryo quality to pregnancies may be used for determinating the embryo quality.

In the development of an embryo the stage of a blastocyst is reached. A blastocyst is an embryo that has developed for five to seven days after fertilisation. At this point the embryo has two different cell types and a central cavity. It has just started to differentiate. The surface cells, called the trophectoderm, will become the placenta, and the inner cells, called the inner cell mass, will become the fetus. A healthy blastocyst should begin hatching from its outer shell, called the zona pellucida by the end of the sixth day. Within about 24 hours after hatching, it should begin to implant into the lining of the mother's uterus.

Microscopic examination of the oocyte may detect abnormalities such as vacuolization, cytoplasmic inclusions, and clustering of organelles. These oocytes will have a poor likelihood of yielding embryos of normal potential. It is known that oocytes may have nuclear or cytoplasmic abnormalities that are not visible in the clinical setting by light microscopy. The most common genetic oocyte abnormality results from an error in chromatid segregation in the first meiotic division. The oocytes with poor quality is discarded, while the oocytes with good quality is cultured.

Embryo transfer

In most in vitro fertilisation programme embryos are transferred to the uterus 2 days after fertilisation (4-8 cells). One view is that the use of embryos at this early stage may contribute significantly to the low pregnancy outcome of IVF programs, and that it is more desirable to use embryos at the blastocyst stage reached at day 5-7 of culture. The advantages suggested include improved synchronisation between embryo and uterus and the ability to select better quality embryos over the longer culture period. Blastocyst transfer may also help reduce the number of multiple births resulting from IVF, through allowing the selection of fewer numbers of highly competent embryos per transfer.

Implantation of the embryo into the uterine wall thus occurs 2-10 days after fertilisation. Within implantation, the embryo connects to the maternal blood supply and is now able to grow. At implantation, the woman's body becomes pregnant for the first time. Prior to implantation, the body is unable to detect the difference between an unfertilised egg (on its way out) or a developing embryo.

One or more pre-embryos suspend in a drop of culture medium are drawn into a transfer catheter, which is guided to the cervix and deposits the fluid into the uterine cavity. One or more embryos may be transferred during this procedure.

The blastocyst culture and transfer procedure for in vitro fertilisation is another method for transfer of embryos to the uterus of the mother. With blastocyst embryo transfer, fewer embryos can be transferred—reducing risks for multiple pregnancy—while keeping overall pregnancy rates high.

The ultimate goal of in vitro fertilisation (IVF) and embryo culture is to provide high quality embryos which are capable of continued normal development and result in live births. However, under standard IVF culture conditions, only about 20-40% of human embryos will progress to the blastocyst stage after 5 days of culture. This low rate of embryo development is the result of a less than optimal culture environment for the embryos. For this reason, embryos have usually been transferred into the uterus after only 2-3 days of culture.

One problem with this is that 2 to 3-day-old embryos are normally found in the fallopian tubes, not in the uterus. The embryo first moves into the uterus at about 80 hours after ovulation. The implantation process begins about 3 days later—after blastocyst formation and hatching have occurred. Therefore, if in vitro culture conditions could be improved so that blastocysts formed at a higher rate, then embryos could be placed into the uterus at the blastocyst stage—at a more "natural" time, and shortly before implantation should occur.

Transferring blastocysts following IVF also provides another benefit—reduction of the possibility of multiple pregnancy. Some 2 or 3-day-old embryos do not have the capacity to become high quality blastocysts and a viable pregnancy. However, on day two or three of culture we do not have reliable methods to determine which embryos will be viable long-term. By culturing embryos to the blastocyst stage we have more opportunity to choose the most competent ones for transfer. We can then transfer fewer embryos and obtain high pregnancy rates with less risk for high order (triplets or higher) multiple pregnancy.

In an embodiment the step a) is conducted at an oxygen tension below 15% and with other conditions as described herein above.

In an embodiment the step b) is conducted at an oxygen tension below 15% and with other conditions as described herein above.

In an embodiment the step a) and b) are conducted at an oxygen tension below 15% and with other conditions as described herein above.

In an embodiment the step a) and c) are conducted at an oxygen tension below 15% and with other conditions as described herein above.

In an embodiment the step a) and d) are conducted at an oxygen tension below 15% and with other conditions as described herein above.

In an embodiment the step b) and c) are conducted at an oxygen tension below 15% and with other conditions as described herein above.

In an embodiment the step b) and d) are conducted at an oxygen tension below 15% and with other conditions as described herein above.

In an embodiment the step a), b) and c) are conducted at an oxygen tension below 15% and with other conditions as described herein above.

In an embodiment the step a), b) and d) are conducted at an oxygen tension below 15% and with other conditions as described herein above.

In an embodiment the step a), c) and d) are conducted at an oxygen tension below 15% and with other conditions as described herein above.

In an embodiment the step b), c) and d) are conducted at an oxygen tension below 15% and with other conditions as described herein above.

In an embodiment the step a), b), c) and d) are conducted at an oxygen tension below 15% and with other conditions as described herein above.

Culture Conditions

The in vitro culture method including the steps a), b), c) and d) or e) and the transfer of the embryo to the uterus as described above are conducted under aseptic conditions. Media and instruments are sterilised before use.

The oxygen tension can be lowered as described formerly where the cultures can be conducted to oxygen tension below 20%, such as 15%, such as below 13%, such as below 11%, such as below 10%, such as below 9%, such as below 8%, such as below 7%, such as below 6%, such as below 5%, such as below 4%, such as below 3%, such as below 2%, such as below 1%. The oxygen tension is regulated by adding oxygen, nitrogen, carbon dioxide, helium or another inert gas or a mixture of two or more of these gasses to the environment of the in vitro culture.

A preferred embodiment of the invention is the culturing conditions of oocyte, spermatozoa and embryo comprising a temperature of 30-45° C., such as 32-42° C., such as 34-40° C., such as 36-38° C., such as 36.5-37.5° C., such as about 37° C. In a preferred embodiment the culturing conditions of oocyte, spermatozoa and embryo comprises a temperature of about 37° C.

Unfortunately in standard culture media the majority of embryos (about 75%) fail to develop beyond the 4-8 cell stage. Nevertheless with certain clinical indications implantation of human embryos is performed at the blastocyst stage despite the low proportions of embryos that develop to blastocyst. Some studies have used co-culture techniques whereby embryos are co-cultured with feeder cells, for example Vero cells, which technique can more than double blastocyst formation. There have been a number of studies using these co-culture techniques which have shown increased implantation rates after blastocyst transfer, particularly in women with repeated previous implantation failures.

Some of the difficulties in assisted reproduction technologies can be overcome by co-culturing sperm, oocytes and embryos with cell feeder layers. However, co-cultures are of variable quality and variable reliability and add the risk of pathogen transfer from the feeder cells to the gametes or embryos that are to be transferred back to living animals or humans. In a preferred embodiment the oocyte and spermatozoa are co-cultured without cell feeder layer.

Small scale in vitro production, i.e. maturation, fertilisation, growth, propagation etc. of sensitive cells and tissues is usually effected in receptacles like small culture flasks, petri- or well-dishes provided with the culture medium and the necessary initial cells or tissues. The receptacles are then placed in an incubator which provide for a selected constant temperature and an environing atmosphere containing the gases necessary for development and/or maintenance of the particular cells or tissues concerned. In particular the necessary gases comprise humidity (i.e. water vapor), free oxygen ($O_2$) and carbon dioxide ($CO_2$) in specific proportions and levels.

By controlling the temperature of the environment as well as the $CO_2$ content, the pH of the culturing medium Can be stabile within a period of time. A stabile temperature together with a stabile $CO_2$ content result in a stabile pH.

In an embodiment of the invention the oocyte and spermatozoa are cultured in medium known to the person skilled in the art. This may be a single medium or different media according to the stage of the oocyte or spermatozoa. The oocyte and spermatozoa may also be cultured in medium modified to the conditions of lowered oxygen tension. The modification may be physical of chemical, in the latter case e.g. by utilising an oxygen molecule carrier or a catalase.

An embodiment of the invention is to apply culture conditions for the oocyte and embryo to provide formation of an increased number of inner cells of the embryo. An increased number of inner cells constitute an embryo of better quality.

Another embodiment of the invention is culturing oocyte and spermatozoa and transferring the resulting pre-embryo to the uterus of a mammalian female, more precisely to the uterine tube of the female uterus. Said transfer may follow a female hormone treatment. Hopefully said transfer lead to pregnancy of the female.

The method described improves the frequencies of succesfull embryo transfer to the female uterus bringing along an increased frequency of pregnancies. In this way the treatment of childlessness is optimised.

When co-culturing of oocytes and spermatozoa are performed at an oxygen tension below 15% this brings about gametes and pre-embryo of a better quality. Also co-culturing of oocytes and spermatozoa at variable oxygen tension below 15% brings about gametes and pre-embryo of a better quality. Gametes and pre-embryo of better quality improve the treatment of childlessness.

When co-culturing of oocytes and spermatozoa are performed at variable oxygen tension this brings about gametes and pre-embryo of a better quality.

A possibility when using the method is co-culturing of oocytes and spermatozoa performed at variable oxygen tension optionally below 15% bringing about gametes and pre-embryo of a better quality and hereby improving the number of inner cells and optimising the cultivation of stem cells.

In an embodiment the cell culture is cultured with increasing oxygen tension, starting with the lowest oxygen tension for the gametes and increasing through the culture of the embryo and blastocyst. The more cells a single structure such as a blastocyst is composed of, the higher oxygen tension is needed.

In an embodiment the cell culture is cultured with increasing oxygen tension, starting with the lowest oxygen tension for the gametes and increasing through the culture of the embryo and blastocyst, and a short increase in the oxygen tension to 10-12% is performed to the oocyte to promote the maturing process.

The improved quality of embryos when culturing as described above may increase the success of embryo transfer from about 20% to at least 25%, such as at least 30%, for example at least 35%, such as at least 40%.

Incubator

The culturing of oocytes, spermatozoa and embryos as described above herein or other biological materials such as cell culture or tissue culture can be performed In an incubator.

The incubator of this invention provide controlled environment for maintaining cell cultures such as oocytes, spermatozoa and embryos in vitro during culturing, examination and manipulation. More particularly the incubator can eliminate conditions which may be toxic or hampering to the cell culture systems.

An embodiment of the invention includes a system capable for in vitro producing a mammalian pre-embryo comprising means for obtaining a mammalian oocyte, and means for obtaining a mammalian spermatozoa, and an apparatus having at least two separate air-tight chambers, for which the oxygen tension of one chamber may be changed independent of the oxygen tension of the other chamber, one of said chambers constitute a main chamber and another of said chambers constitute at least one residence chamber, said apparatus comprising at least one entrance port capable of communicating with the means for obtaining the mammalian oocyte and/or the mammalian spermatozoa, and an exit port for withdrawal of the pre-embryo, as well as a communication port between said at least two chambers allowing transfer of oocyte, spermatozoa and/or pre-embryo between the chambers.

The main chamber comprises a working area for handling the cell cultures. The main chamber includes equipment for the cell culture handling e.g. containers with culture medium. The main chamber can also include further equipment for the cell culture handling e.g. microscope, ICSI apparatus. From the main chamber there is connection to an entrance chamber or exit port. In particular the main chamber is not an entrance chamber. In particular the main chamber is not a residence chamber.

A residence chamber is a chamber for one or more culture containers, the culture container can itself be a residence chamber. The residence chamber is connected with the main chamber or placed within the main chamber. In particular the residence chamber is not an entrance chamber or exit port.

In an embodiment of the invention the incubator provides means for controlling temperature, humidity and $O_2$-concentration. It excludes micro organism from the environment obtaining aseptic conditions within the incubators if desired by using laminar air flow.

The oxygen tension or oxygen concentration within the chambers can be controlled. The oxygen tension can be determined by sensing means. Further the oxygen tension can be sustained or changed within the chambers by adding gas such as oxygen, nitrogen, carbon dioxide, helium or another inert gas, or a mixture of two or more of these gasses. Thus the incubator contribute means for adding said gasses. In the controlling, sustaining and changing of the oxygen tension, said oxygen tension within the chambers can be obtained independently in each chamber at a level of 0.1 to at least 21%. A preferred oxygen tension can be at a level of 0.5 to 15%. The temperature and humidity of the chambers can be measured and regulated by measuring means and supplying means in accordance to a predetermined minimum level and maximum level of each of the gasses, of the temperature and of the humidity. The supplying means can constitute means allowing inlet of gas or gas containing water (humidity) whereas the supplying means also can constitute heaters or coolers.

In an embodiment of the system, the gas directed to any chamber of the incubator is humidified by circulated through a humidificator before entering a chamber of the incubator. Said gas can also be heated or cooled in a heater or cooler before entering a chamber of the incubator.

An embodiment is the system wherein the means for obtaining a mammalian oocyte is a system with a needle communicating under airtight conditions with a means for transferring from needle to said apparatus, such means for transferring comprises syringe optionally connected to a tube.

Another embodiment of the invention is a system wherein the means for obtaining a mammalian spermatozoa is a system in which the oxygen tension can be controlled. Said system can be a syringe optionally air-tight and further optionally connected to a tube.

By performing the invention utilising the above mentioned needle in combination with control or oxygen tension, the oocyte can be harvested at conditions including a lowered oxygen tension as described above herein.

In an embodiment of the system the temperature of each chamber can be regulated independently.

In another embodiment of the system the oxygen tension of each chamber is regulated independently by adding oxygen, nitrogen, carbon dioxide, helium or another inert gas, or a mixture of two or more of these gasses simultaneously with removing gas from the chambers, in the way that the pressure of the atmosphere inside the chamber is in accordance with the atmosphere of the outside of the incubator.

In yet another embodiment of the system the pressure of the gasses inside the chambers is slightly higher than the pressure of the atmosphere surrounding the main chamber.

A high humidity is necessary within the chambers to prevent excessive evaporation of the culture medium in which the cell cultures such as oocytes, spermatozoa and embryos are cultured or maintained. A preferred embodiment of the system is an incubator wherein the humidity of each chamber, is independently regulated to a level between 50% and 100%, such as between 60% and 99%, for example between 70% and 98%, more preferred between 80% and 97%, such as between 70% and 96%, for instance between 80% and 95.5%, most preferable between 90% and 95%.

Most cultures of biological material are maintained at a temperature of 10-50° C. In a preferred embodiment of the invention the temperature in the incubator is regulated for the culturing of oocyte, spermatozoa, embryo, and stem cells including stem cell lines comprising a temperature pre-selected between 30-45° C., such as 32-42° C., such as 34-40° C., such as 36-38° C., such as 36.5-37.5° C., such as about 37° C. In a preferred embodiment the culturing conditions of oocyte, spermatozoa, embryo and stem cells including stem cell lines comprises a temperature of about 37° C.

In another embodiment the temperature of each chamber of the incubator is controlled and regulated independently in accordance to the above mentioned temperatures, in a way where a heater is turned on if the temperature is lower than e.g. 0.2 degree of a pre-selected temperature. A cooler may turn on if the temperature is higher than e.g. 0.2 degree of a pre-selected temperature. The heater or cooler turn off when the pre-selected temperature within the actual chamber is reached.

In a preferred embodiment of the system the entrance port and the exit port is combined to a single opening means, such as a door.

In a more preferred embodiment of the system the entrance port and the exit port is combined in a means for transporting cell culturing means and equipment to and from the outer chamber. Preferred is a system wherein said combination of the entrance port and the exit port is an air lock. More preferred is a system wherein the entrance port constitute an inner door of the air lock and the exit port constitute an outer door of the air lock. Also preferred is a system wherein said air lock comprises walls between the inner door and the outer door constituting a small air-tight chamber.

In an embodiment of the system the inner door and the outer door of the air lock only can be opened one at a time in the way that only one door can be open at a time, and the opening of one door can only set going when the other door is totally shut. No gas inlet in the air lock can be performed when the outer door is open.

In an embodiment of the system the atmosphere of the air lock can be controlled and adjusted including contents of oxygen, nitrogen, carbon dioxide, helium or another inert gas, temperature and humidity. The atmosphere of the air lock can be regulated through regulation means by-adding oxygen, nitrogen, carbon dioxide, helium or another inert gas or a mixture of two or more of these gasses. The temperature and humidity of the air lock can also be regulated through regulation means by activation a heater or cooler or by supplying humidity. The regulation of gas concentrations, temperature and humidity can be performed in accordance to measurements executed by measuring means positioned in the air lock. The supply of the mentioned gasses can be performed in accordance to a predetermined level, the temperature and humidity can also be regulated in accordance to a predetermined level. In a preferred embodiment the atmosphere in the airlock is regulated to be similar to the atmosphere of the main chamber in accordance to gas concentrations, temperature and humidity.

In an embodiment of the system the inner door of the air lock only can open when the conditions including temperature, humidity and contents of oxygen is equal to the conditions inside the chamber which the air lock is positioned inside.

In an embodiment of the system a tray is placed in the air lock. The tray performs an easier entrance and exit for containers, handling objects and other equipment.

Between the working area of the incubator and the outside of the incubator, an airlock is positioned, reducing the risk of altering the conditions (temperature, humidity, $O_2$-concentration) in the working and depository areas. Between the airlock and the outside of the incubator is the outer door of the airlock, between the airlock and the working area of the incubator is the inner door of the airlock. All objects and media transported to the working area from outside can pass the airlock in the way that the inner door of the air lock is closed, the outer door of the air lock is opened, the objects is placed in the airlock, the airlock is closed. The environment in the air lock is adjusted to similar conditions as in the working area, when said conditions is obtained, the inner door of the air lock can be opened, and the objects can be transferred to the working area. The transport of objects from the working area to the outside of the incubator is performed by closing the outer door of the airlock, adjusting the airlock to similar conditions as in the working area, when said conditions is obtained, the inner door of the airlock can be opened, and the objects can be transferred from the working area to the airlock, the inner door of the airlock is closed, the outer door of the airlock is opened and the objects is transported to the outside of the incubator. A controlling mean only permit one door of the airlock to be open at a time. An alarm comprising a lamp flashing on and off or a sound will indicate when the inner part of the airlock is about to be opened and the conditions in the airlock is not similar to the conditions in the working area.

In another embodiment of the system a microscope can be placed and used when handling the oocytes, spermatozoa, embryos and stem cells including stem cell lines. The microscope may be a binocular microscope. The working area of the microscope where culturing dishes to monitor are placed is situated inside the main chamber. The microscope extends through an aperture in the top of the main chamber preferable in a way making it comfortable for a user working with the cell cultures inside the incubator and optionally connected to a monitoring screen. The aperture contains sealing means sealing the annulus between the edge of the main chamber and the microscope thereby minimising or avoiding leakage between the main chamber and the external of the incubator. The sealing means may perform flexible plastic cuff.

The microscope may be connected to a camera, said camera can be adjusted to obtain images of the cell or cells in culture, the images can be taken manually or automatic with predetermined intervals. The images are stored, preferred is electronic storage within a computer. The images can be used as described below.

In a preferred embodiment of the system a working area is obtained within the main chamber, the working area comprises a place for culturing means containing the cultured cell structures, where the cultured cell structures is observed in the microscope, and said working area comprises room for handling means.

In another preferred embodiment of the system the main chamber comprises opening means or apertures or hand openings permitting entrance to human hands to handle the cell culture or the equipment inside the chambers.

In an embodiment of the system the opening means or apertures or hand openings are attached gloves or gloves without fingers. These gloves or gloves without fingers are mounted in the way that human hands can fit into the gloves or gloves without fingers and handling the cell culture or the equipment inside the chambers. The glove or the fastening area between the incubator and the gloves or gloves without fingers do not permit any organisms such as virus, fungus and bacteria to penetrate from the outside to the inside of the incubator or vice versa, or at least the penetration of gasses through these openings or apertures is minimized by mounting sealing means between the gloves and the main chamber wall. Handling the Petri dishes inside the incubator is performed by sticking the hands inside the gloves or gloves without fingers. If desired, the surface of said glove which is positioned inside the incubator is sterilised before use.

In another embodiment the opening means comprises apertures where a stream of gas directed away from the incubator or directed parallel to the wall containing the opening means can be obtained. The gas can be air, nitrogen etc. The gas can be turned off when the apertures are not used and the apertures can be closed by a lock. The stream of gas prevents air to enter into the incubator.

To the opening means or apertures sticks, bars or instruments can be attached, said sticks, bars or instruments can be manipulated by fibre optics, and further the cell culture or the equipment to be handled can be handled by said sticks, bars or instruments.

In an embodiment of the system, the incubator has a door in the rear of the main chamber permitting the insertion of larger objects, such as the microscope into the main chamber. The at least one residence chamber is each controlled individually in a way that opening of the main chamber do not influence the culturing conditions inside the at least one residence chamber.

In an embodiment of the system the main chamber has at least one small part of its surface replaced with a membrane, said membrane has a structure through which a needle can be stuck through, when the needle is removed said membrane fills up the area where the needle was stuck through, and no gasses or particles can diffuse through the membrane either when a needle is stuck through the membrane or no needle is stuck through the membrane.

In an embodiment of the system the at least two separate chambers are arranged as a main chamber and one or more smaller air-tight residence chambers. Preferred is a system where the smaller residence chambers are located inside the main chamber or are attached to the main chamber. Also preferred is a system where the residence chambers are air-tight and can be controlled independent of each other and independent of the main chamber according to temperature, humidity, and contents of oxygen, nitrogen and carbon dioxide. More preferred is a system wherein the residence chambers constitute boxes for culture containers containing cell cultures of oocyte, spermatozoa, embryo, and stem cells including stem cell lines. The boxes constitute culture chambers or storage chambers for the cell cultures. Also preferred is a system where each box is adapted for receiving one culture container containing the cell cultures. Another preferred system is a system wherein the number of the boxes correspond to the number of development stages of the cell cultures.

In an embodiment the system wherein the cell culturing is performed comprises the development stages of at least Immature oocyt, Mature oocyt, Immature Spermatozoa, Mature Spermatozoa, Fertilised oocyt, 2 cell embryo, 4 cell embryo, 8 cell embryo, Morula, Blastocyst, stem cells and stem cell lines.

In an embodiment of the system the oxygen tension and pressure of each residence chamber can be regulated by a computer by retrieving an image of the embryo in said chamber or said air-tight boxes. The image is retrieved by a camera. The camera may by manually connected to each of the air-tight boxes, or it moves from box to box automatically or a camera .s permanently connected to each box, or the air-tight boxes moves to the camera in a way where the boxes are mounted in a carousel or the boxes are mounted on a system which moves the boxes around e.g. a rail system. The camera permanently connected to each cell culture container can be e.g. a chip, a CCD camera or a small camera in a foil.

In another embodiment an image of the culture is send to the computer in intervals of at least 1 minute, such as at least 5 minutes, such as at least 10 minutes, such as at least 20 minutes, such as at least 40 minutes, such as at least 1 hour, such as at least 2 hours, such as at least 4 hours, such as at least 6 hours, such as at least 8 hours, such as at least 12 hours, such as at least 18 hours, such as at least 24 hours.

The images may be compared to a series of pre-stored images, said pre-stored images together comprising almost movies of different developmental routes including routes resulting in blastocysts and/or stem cells and/or stem cell lines of good quality, middle quality, poor quality and routes leading to cell death. The pre-stored images are by a computer programme connected to information comprising culturing conditions. By comparing the images of a gamete or cell in culture with the prestored images it can be determined by the computer programme whether the culturing conditions should be changed to obtain a blastocyst, stem cell or stem cell line of the best quality obtainable or of a pre-determined quality.

Changing the culturing conditions including e.g. temperature and oxygen tension may be done manually or automatically. For the manually changing of the culturing conditions an indicator such as a flash or a highlighted line on a monitoring screen may indicate when the computer programme has found a residence chamber where the culturing conditions should be changed. The changing of e.g. the oxygen tension may be a short period with a lowered or increased oxygen tension to trigger the development of the cell, or a prolonged change in the oxygen tension to obtain specific culture condition.

In an embodiment of the invention the culturing conditions further including composition of the culture medium can be changed manually or automatically due to a response when combining an image of the cell in culture with pre-stored images as described above.

Preferred is when the medium is changed 1-4 times in the process from gametes to blastocyst. More preferred is 1-3 changes of medium. Most preferred is 1-2 changes of medium.

In an embodiment of the invention the pre-stored images and the different developmental routes as described above comprises an environment controlling programme for a computer. The programme controls the environment including temperature, gasses and/or media as described elsewhere by combining an image of a cell in culture with the pre-stored images.

In an embodiment the environment controlling programme is used when a cell culture is initiated. The environment controlling programme is activated either by manually typing in the developmental stage of the cell, or an image of the cell activates the environment controlling programme.

In an embodiment the culture room in the culture containers are bowl-shaped with a smaller bottom than the opening in a way that in said smaller bottom the cell to be cultured is within a limited area optimising the focusing of the camera when obtaining an image and utilising this image as described elsewhere.

In an embodiment the culture containers comprises at least one tube mounted to the bowl-shaped culture room. Through said at least one tube gasses or medium can be changed, instruments can be connected e.g. thermometer or instruments for obtaining other measurements e.g. compound concentration of the medium or osmolarity of the medium. The lid for each culture room can be the camera or the camera can be incorporated into or mounted directly to the lid. The lid can also comprise steering means for directing the camera to the right position. Said steering means can be but are not limited to at least one vertical sticks optionally with a notch or horizontal sticks optionally with a notch which secure the camera or an attachment of the camera.

In an embodiment the culture containers and/or the culture rooms are composed of a material protecting the cells from light. If the material excludes light, the lid can be of a light-sensitive material to secure the possibility to use a microscope or camera to observe the cell. If the material do not excludes light, the culture containers can be protected from light by a residence chambers that excludes light, or the culture containers can be protected from the light of the incubator or from the light from the outside of the incubator by any hiding method.

In an embodiment the culture containers comprise the residence chambers, and comprise the features of the residence chambers and air-tight boxes as described elsewhere herein.

In an embodiment the incubator comprises an ICSI system to perform the ICSI as described elsewhere herein.

In an embodiment of the system the residence chambers are air-tight boxes, which are portable. Preferred is a system with the air-tight boxes which when removed from the apparatus can be connected to means for controlling temperature, humidity, and contents of oxygen, nitrogen and carbon dioxide. Also preferred is a system wherein the means for controlling temperature, humidity, and contents of oxygen, nitrogen and carbon dioxide is portable. Further preferred is a system wherein the wall of the air-tight boxes contains a membrane. Yet further preferred is a system wherein the air-tight boxes comprises fastening means for fastening one or more cell culture containers. Also preferred is a system wherein the wall of the cell culture containers contain a sterile membrane. In an embodiment of the system the air-tight boxes can be transported for at least 6 days.

In an embodiment of the system the dimension of the main chamber is between 1 cm and 2 m, such as between 20 and 50 cm, such as between 50 and 70 cm, such as between 70 and 90 cm, such as between 90 and 110 cm, such as between 110 and 130 cm, such as between 130 and 150 cm, such as between 150 and 170 cm, such as between 170 and 200 cm. Preferred is longitudinal chambers with the depth of between 50 and 110 cm, such as between 50 and 70 cm, such as between 70 and 90 cm, such as between 90 and 110 cm, and the length of between 50 and 200 cm, such as between 50 and 70 cm, such as between 70 and 90 cm, such as between 90 and 110 cm, such as between 110 and 130 cm, such as between 130 and 150 cm, such as between 150 and 170 cm, such as between 170 and 200 cm and a height of between 50 and 110 cm, such as between 50 and 70 cm, such as between 70 and 90 cm, such as between 90 and 110 cm.

Stem Cells

In another aspect the invention relates to an embryonal stem cell composition. The method improve the number and quality of inner cell mass of blastocyst, which further gives an improvement of number and quality of stem cells derived from the inner cell mass.

In an embodiment the stem cells are more stable than convenient stem cells. The stem cells may be obtained for a period in an undifferentiated stage. In an embodiment said undifferentiated stage of stem cells are maintained by culture conditions including an oxygen tension below 15%.

In an embodiment is a method of producing a stem cell, said method comprises:
   a) Providing a multicellular pre-embryo as described elsewhere herein,
   b) isolating a multicellular pre-embryo of a),
   c) isolating cells from the inner cell mass of the pre-embryo of b),
   d) culturing said isolated cells from the inner cell mass in a matrix gel,
   e) obtaining stem cells.

In an embodiment at least one of the steps b), c), d), and e) is conducted at an oxygen tension below 15%. In another embodiment at least two of the steps b), c), d), and e) are conducted at an oxygen tension below 15%. In a further embodiment at least three of the steps b), c), d), and e) are conducted at an oxygen tension below 15%. In yet a further embodiment all of the steps b), c), d), and e) are conducted at an oxygen tension below 15%.

Another aspect is a stem cell obtained from cell cultures as defined herein above. From said stem cell stem cell lines can be obtained.

In an embodiment the period for which the stem cells are maintained in an undifferentiated stage is at least 4 hours, such as at least 8 hours, for example at least 12 hours, such as at least 24 hours, for example at least 2 days, such as at least 3 days, for example at least 4 days, such as at least 5 days, for example at least 7 days, such as at least 9 days, for example at least 11 days, such as at least 13 days for example at least 15 days, such as at least 20 days, for example at least 25 days, such as at least 30 days.

In an embodiment the period for which the stem cells are maintained in an undifferentiated stage is at least 1 month, such as at least 1½ month, for example at least 2 months, such as at least 3 months, for example at least 4 months, such as at least 5 months, for example at least 6 months, such as at least 7 months, for example at least 8 months, such as at least 9 months, for example at least 10 months, such as at least 11 months, for example at least 12 months.

In an embodiment the period for which the stem cells are maintained in an undifferentiated stage is at least 1 year, such as at least 1½ year, for example at least 2 years, such as at lease 2½. years, for example at least 3 years, such as at lease 3½ years, for example at least 4 years, such as at lease 4½ years, for example at least 5 years, such as at lease 6 years, for example at least 7 years, such as at lease 8 years, for example at least 9 years, such as at lease 10 years, for example at least 1 years, such as at lease 12 years, for example at least 13 years, such as at lease 14 years, for example at least 15 years, such as at lease 20 years.

The stem cells are stabile in the period for which they are maintained in the undifferentiated stage, in the sense no mutations or other genetic changes occur within the chromosomes or antigenesity on the surfaces of the cells. The stem cell lines are free of pathogens, they are well characterised as the human sources are known, and the culture conditions for the gametes and/or the embryo and/or blastocyst are known.

In an embodiment the stem cells and/or stem cell lines are propagated on a matrix gel and/or with feeder cells. The extracellular matrix can be synthetic or derived from animal/human material with the object of supporting stemcell anchoring, cleaveages, and ensuring both dedifferentiation, differentiation or keeping them undifferentiated according to supplements or ingredients within the matrix.

The stem cell lines produced from the stem cells are stabile in the sense no mutations or other genetic changes occur within the chromosomes or antigenesity on the surfaces of the cells. The stem cell lines are free of pathogens, they are well characterised as the human sources are known, and the culture conditions for the gametes and/or the embryo and/or blastocyst are known.

Each stem cell line is provided with a certificate indicating the origin of the cell line, the characteristics of the cell line including types of antigens at the surface of the cells, and a recipe to control the further development of the cell line into differentiated cells.

Another aspect is a stem cell package comprising:
   Stem cells as defined herein above,
   Certificate describing the culture conditions for the stem cells and the cell cultures from which said stem cells are obtained.

In particular the certificate describes that the cells have been cultured at an oxygen tension below 15% in at least a part of the steps a) to e) described above for the production of multicellular pre-embryos. Preferred is at a lower oxygen tension as described above. Included with the certificate can be a recipe to control the further development of the cell line into differentiated cells.

DETAILED DESCRIPTION OF THE DRAWINGS

FIG. 1 illustrates an embryo scoring system. The development of an embryo is shown from the top. The score or development is as follows:
Score 1.0: Equally-sized symmetrical blastomers, no anuclear fragments.
Score 2.0: Uneven sized blastomers, no anuclear fragments.
Score 2.1: Embryos with less than 10% fragmentation.
Score 2.2: Embryos with 10-20% blastomeric fragmentation.
Score 3.0: Embryos with 20-50% blastomeric fragmentation.
Score 3.2: Embryos with more than 50% blastomeric fragmentation.
Score 4.0: Totally fragmentised.
Score 5.0: Fertilised, not separated.
Score 6.0: Not fertilised, not separated.
M: Morula.
B1: Early blastocyst.
B2: Expanding blastocyst,
B3: Expanded blastocyst.
Bn1: Normal cavity, normal cells.
Bn2: Normal cavity, granular or dark cells.
Bn3: Anormal cavity.
HB1: Hatching blastocyst.
HB2: Hatched blastocyst.

FIG. 2 illustrates a cumulative embryo scoring (CES) system. This is an example of points given to the embryo of different developmental stages. FIG. 2a is an embryo with equal number of blastomeres formed and no fragment, and is given 4 points. FIG. 2b is an embryo with uneven number of blastomeres with less than 10% fragments, and is given 3 points. FIG. 2c is an embryo with uneven number of dissimilar blastomeres and 10-50% fragmentation. FIG. 2d is an embryo with scarcely recognizable blastomers with >50% fragmentation, and is given 1 point.

Figure 3:
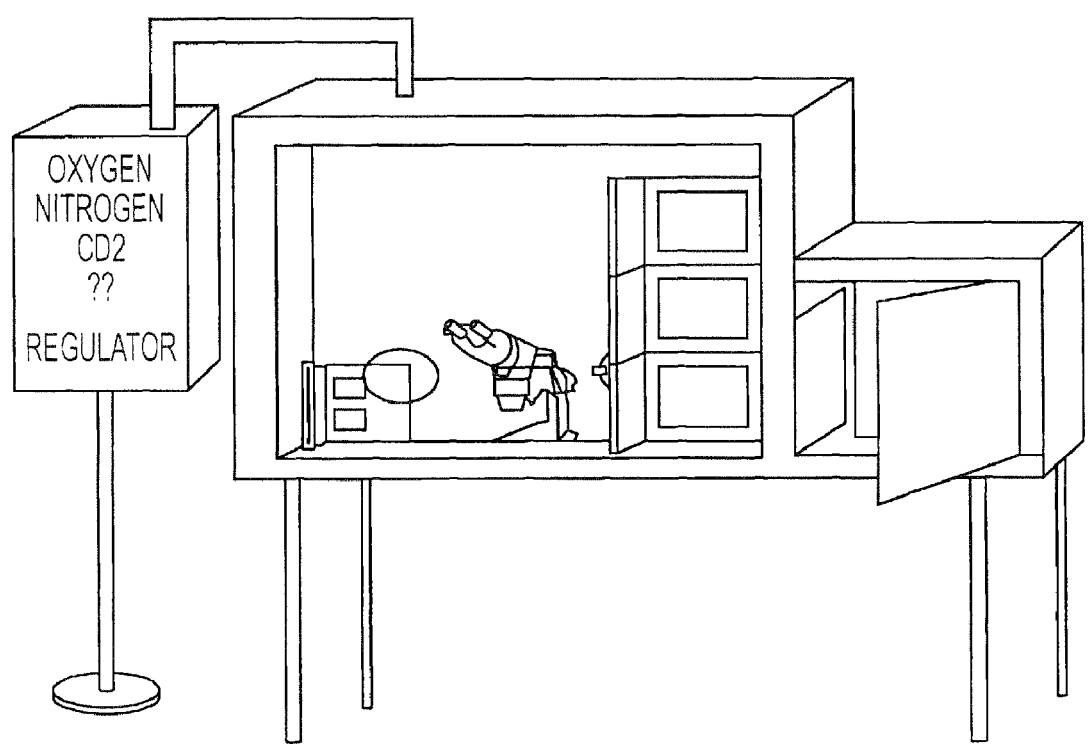
FIG. 3 illustrates an incubator.

FIG. 3 illustrates an incubator. The incubator is equipped with an air-lock, a regulator for oxygen, nitrogen, carbon dioxide and other gasses as well as the temperature. In the incubator a microscope and air tight boxes is placed.

EXAMPLE

Effect of low oxygen tension on oocyte quality, embryonic development in human ova during in vitro maturation, in vitro fertilisation and embryo development.

The following example is conducted at the Section for reproductive biology, at Herlev University Hospital, where currently more than 500 IVF cycles and 200 IVM cycles per year is carried out. A study addressing 2 aspects of human in vitro fertilisation treatments is conducted.
 1) Does low oxygen tension benefits routine IVF
 2) Does low oxygen tension benefits IVM treatments.

The cultures and handling of all gametes and embryos from the time of oocyte collection to embryo transfer takes place either in the normal routine laboratories and incubators or for the period in the culture box (see description below).

The culture box:

The culture box comprises a sealed culture box with multifunctional porthole systems used for operating the in vitro cultures. The atmosphere should be a 5% $CO_2$ on a 5% $O_2$ in a humidified atmosphere. The temperature should be 37.2° C., and the atmosphere and box should be sterile. An airlock should be attached.

By using such a system change in oxygen tension and carbon dioxide can be avoided, and a better culture results could be expected according to already published data.

Study set up

Study 1:

200 routine IVF cycles are randomly allocated to either culture in the culture box at 5% oxygen tension in 5% $CO_2$ or in our routine incubators at 20% oxygen and 5% $CO_2$.

This will provide app. 600 embryos in each group and the following data are collected:
No. Fertilised ova,
No. Cleaved ova,
Embryo quality,
No. Transferable embryos,
No. Frozen embryos,
No. gestations,
Implantation rate.

Study 2:

100 IVM cycles are randomly allocated to either culture in the culture box at 5% oxygen tension in 5% $CO_2$ or in our routine incubators at 20% oxygen and 5% $CO_2$.

This will provide app. 100 embryos in each group and the following data are collected:
No. ova with GVBD
No. MFII oocyte,
No. Fertilised ova,
No. Cleaved ova,
Embryo quality,
No. Transferable embryos,
No. Frozen embryos,
No gestations,
Implantation rate.

Results

All patients fulfilling the inclusion criteria for the trial are asked for informed consent during their treatment for infertility at the clinic.

After the informed consent are given, the patients are randomized either to have their embryos cultured in the conventional regime at 20% oxygen or to the test regime with 5% oxygen. Oocytes are removed from the ovarian with a syringe, hereby obtaining the normal oxygen tension of the ovarian.

5% culture of embryos:

The day before embryo pick-up, the culture media are prepared by being incubating in the low oxygen environment.

At the embryo pick-up day, the sperm is prepared and immediately hereafter incubated in order to be equilibrated for the fertilization later.

After the embryo pick-up, the embryos are identified and immediately put into the incubated media and incubated in the 5% oxygen environment.

In the afternoon the embryos are fertilized and hereafter removed to another culture dish.

The fertilized embryos remain in the low oxygen environment until they are supposed to be transferred back. Prior to the transferation all the embryos are scored in order to select the best embryos for the transferation.

The results:

|  | No. of aspirated oocytes | No. of cleaved oocytes | No. of oocytes qualified for transferation | No. of pregnancies (pregnancies of implantation) |
|---|---|---|---|---|
| Incubator | 86 | 58 (67.4%) | 43 (50%) | 4 of 9 (44.4%) |
| Control | 122 | 81 (66.4%) | 64 (52.5%) | 3 of 13 (23.1%) |

REFERENCES

Fisch, J. D., H. Rodriguez, R. Ross, G. Overgy & G. Sher. The Graduated embryo score (GES) predicts blastocyst formation and pregnancy rate from cleavage-stage embryos. Human Reproduction vol 16, no. 9, pp. 1970-1975, 2001.

Joesbury, K. A., W. R. Edirisinghe, M. R. Phillips & J. L. Yovich. Evidence that male smoking affects the likelihood of a pregnancy following IVF treatment: application of the modified cumulative embryo score. Human Reproduction vol 13 no. 6, pp. 1506-1513, 1998.

Van Abbel et al. Human Reproduction, vol 7, no. 1, pp. 117-119, 1992.

Ziebe, S., K. Petersen, S. Lindenberg, A.-G. Andersen, A. Gabrielsen & A. Nyboe Andersen. Embryo morphology or cleavage stage: how to select the best embryos for transfer after in-vitro fertilisation. Human Reproduction vol. 12, no. 7, pp. 1545-1549, 1997.

The invention claimed is:

1. A method for in vitro producing a mammalian pre-embryo comprising the following steps:
   a1) providing a mammalian oocyte,
   a2) providing a mammalian spermatozoa,
   b) culturing the oocyte and the spermatozoa,
   c) fertilizing the oocyte with the spermatozoa obtaining a fertilized oocyte, and
   d) allowing cell-division of the fertilized oocyte obtaining a multicellular pre-embryo,
wherein at least one of the steps a1) or a2) is conducted at an oxygen tension below 15% and/or wherein at least one of the steps comprises a change in the oxygen tension.

2. The method according to claim 1, wherein the mammalian oocyte and mammalian spermatozoa are gametes obtained from humans.

3. The method according to claim 1, wherein the oocyte is obtained from the ovarium.

4. The method according to claim 3, wherein the oocyte is obtained from the ovarium by aspiration into a needle.

5. The method according to claim 4, wherein said needle is part of a syringe and the oxygen tension within said needle and said syringe is lower than 15%.

6. The method according to claim 1, wherein the spermatozoa is obtained from a male under conditions of an oxygen tension below 15%.

7. The method according to claim 6, wherein the spermatozoa is obtained from semen or testicular tissue.

8. The method according to claim 1, wherein the oxygen tension is below 13.

9. The method according to claim 1, wherein step b) comprises co-culturing the oocyte and the spermatozoa.

10. The method according to claim 9, wherein the co-culturing of oocyte and spermatozoa results in fertilization of oocyte by spermatozoa.

11. The method according to claim 1, wherein the oocyte is fertilised with the spermatozoa by Intracytoplasmic sperm injection (ICSI).

12. The method according claim 1, wherein the fertilised oocyte is cultured to an embryo stage ready for transfer to the female uterus.

13. The method according to claim 1, wherein at least a part of step a) and at least one of the other steps are conducted at an oxygen tension below 15%.

14. The method according to claim 1, wherein at least 3 of the steps a), b), c) and d) are conducted at an oxygen tension below 15%.

15. The method according to claim 1, wherein all of the steps a), b), c) and d) are conducted at an oxygen tension below 15%.

16. The method according to claim 1, wherein the oxygen tension of step d) is higher as compared to the oxygen tension of any of the other steps b) and c).

17. The method according to claim 1, wherein conditions allowing maturation of the oocyte includes a rise in the oxygen tension followed by lowering the oxygen tension.

18. The method of claim 17, wherein the rise of the oxygen tension is at least 1 unit.

19. The method according to claim 1, wherein the oxygen tension is at least 0.5% and maximum 21%.

20. The method of claim 18, wherein the rise of the oxygen tension is maintained for at least 5 minutes.

21. The method according to claim 1 wherein the oxygen tension is regulated in accordance to the phase and the condition of the oocyte or the embryo.

22. A method for implanting a pre-embryo, comprising culturing oocyte and spermatozoa as defined in claim 1, and transferring the resulting pre-embryo to the uterus of a mammalian female.

* * * * *